(12) United States Patent
Taber

(10) Patent No.: US 10,596,354 B2
(45) Date of Patent: Mar. 24, 2020

(54) GUIDE WIRES, CATHETERS, AND GUIDE WIRE CATHETER SYSTEMS AND METHODS

(71) Applicant: Mark Taber, St. Louis, MO (US)

(72) Inventor: Mark Taber, St. Louis, MO (US)

(*) Notice: Subject to any disclaimer, the term of this patent is extended or adjusted under 35 U.S.C. 154(b) by 0 days.

(21) Appl. No.: 15/274,701

(22) Filed: Sep. 23, 2016

(65) Prior Publication Data

US 2017/0087339 A1    Mar. 30, 2017

Related U.S. Application Data

(60) Provisional application No. 62/232,829, filed on Sep. 25, 2015, provisional application No. 62/359,090, filed on Jul. 6, 2016.

(51) Int. Cl.
*A61M 25/09* (2006.01)
*A61M 25/10* (2013.01)

(52) U.S. Cl.
CPC .. *A61M 25/0905* (2013.01); *A61M 25/09041* (2013.01); *A61M 25/10* (2013.01);
(Continued)

(58) Field of Classification Search
CPC combination set(s) only.
See application file for complete search history.

(56) References Cited

U.S. PATENT DOCUMENTS 4,854,325 A    8/1989  Stevens
4,894,051 A    1/1990  Shiber
(Continued)

FOREIGN PATENT DOCUMENTS

EP    0189329 A2    7/1986
EP    0418677 A1    3/1991
(Continued)

OTHER PUBLICATIONS

EP Application No. 08772056: European Search Report dated Mar. 29, 2012.
(Continued)

*Primary Examiner* — Sean P Dougherty
*Assistant Examiner* — Benjamin S Melhus
(74) *Attorney, Agent, or Firm* — Venable LLP; Michele V. Frank

(57) ABSTRACT

Guide wires, systems and methods can improve advancement through the vasculature, particularly when the catheter tip encounters resistance or an obstruction and cannot advance. The guide wire can include an enlargement spaced proximally from a distal tip of the elongated member alone or in combination with a configured portion of the wire. The configured guide wire can be positioned in the vasculature and a medical device such as a catheter can track over the guide wire. The catheter can get caught-up in the vasculature or on implanted devices during advancement. When that occurs, the configured guide wire can be retracted back to the catheter tip and the guide wire configuration can cause the catheter distal tip to move and/or deflect away from the obstruction or resistance allowing the system to advance. The guide wire can be returned to its distal position and the procedure can continue.

48 Claims, 17 Drawing Sheets

(52) U.S. Cl.
CPC .......... *A61M 2025/09125* (2013.01); *A61M 2025/09133* (2013.01); *A61M 2025/09166* (2013.01)

(56) References Cited

U.S. PATENT DOCUMENTS

| | | | |
|---|---|---|---|
| 4,898,575 A | | 2/1990 | Fischell et al. |
| 4,917,094 A | | 4/1990 | Lynch et al. |
| 4,983,165 A | | 1/1991 | Loiterman |
| 5,002,560 A | | 3/1991 | Machold et al. |
| 5,059,183 A | * | 10/1991 | Semrad .............. A61M 25/06 600/585 |
| 5,071,407 A | | 12/1991 | Termin et al. |
| 5,221,261 A | | 6/1993 | Termin et al. |
| 5,295,493 A | | 3/1994 | Radisch, Jr. |
| 5,303,714 A | | 4/1994 | Abele et al. |
| 5,334,166 A | | 8/1994 | Palestrant |
| 5,378,239 A | | 1/1995 | Termin et al. |
| 5,411,033 A | * | 5/1995 | Viera ............ A61B 17/320758 600/434 |
| 5,456,667 A | | 10/1995 | Ham et al. |
| 5,465,733 A | * | 11/1995 | Hinohara .............. A61M 25/09 600/585 |
| 5,480,423 A | | 1/1996 | Ravenscroft et al. |
| 5,484,407 A | | 1/1996 | Osypka |
| 5,496,277 A | | 3/1996 | Termin et al. |
| 5,509,900 A | | 4/1996 | Kirkman |
| 5,514,073 A | | 5/1996 | Miyata et al. |
| 5,575,771 A | | 11/1996 | Walinsky |
| 5,628,761 A | | 5/1997 | Rizik |
| 5,634,897 A | * | 6/1997 | Dance ................ A61B 17/22 604/28 |
| 5,643,298 A | | 7/1997 | Nordgren et al. |
| 5,769,821 A | | 6/1998 | Abrahamson et al. |
| 5,807,236 A | | 9/1998 | Bacich et al. |
| 5,824,055 A | | 10/1998 | Spiridigliozzi et al. |
| 5,824,058 A | | 10/1998 | Ravenscroft et al. |
| 5,902,254 A | * | 5/1999 | Magram .............. A61M 25/09 600/585 |
| 5,908,405 A | | 6/1999 | Imran et al. |
| 5,947,924 A | | 9/1999 | Liprie |
| 6,007,514 A | | 12/1999 | Nita |
| 6,059,812 A | | 5/2000 | Clerc et al. |
| 6,071,263 A | | 6/2000 | Kirkman |
| 6,071,285 A | | 6/2000 | Lashinski et al. |
| 6,113,579 A | * | 9/2000 | Eidenschink ..... A61M 25/0068 604/264 |
| 6,126,649 A | | 10/2000 | VanTassel et al. |
| 6,159,139 A | | 12/2000 | Chiu |
| 6,165,209 A | | 12/2000 | Patterson et al. |
| 6,221,006 B1 | | 4/2001 | Dubrul et al. |
| 6,234,952 B1 | | 5/2001 | Liprie |
| 6,251,132 B1 | | 6/2001 | Ravenscroft et al. |
| 6,371,978 B1 | | 4/2002 | Wilson |
| 6,398,708 B1 | | 6/2002 | Hastings et al. |
| 6,416,523 B1 | | 7/2002 | Lafontaine |
| 6,425,898 B1 | | 7/2002 | Wilson et al. |
| 6,454,775 B1 | | 9/2002 | Demarais et al. |
| 6,520,923 B1 | | 2/2003 | Jalisi |
| 6,544,253 B1 | | 4/2003 | Tanner |
| 6,558,349 B1 | | 5/2003 | Kirkman |
| 6,579,302 B2 | | 6/2003 | Duerig et al. |
| 6,596,005 B1 | | 7/2003 | Kanz |
| 6,660,014 B2 | | 12/2003 | Demarais et al. |
| 6,695,858 B1 | | 2/2004 | Dubrul et al. |
| 6,702,830 B1 | | 3/2004 | Demarais et al. |
| 6,808,531 B2 | | 10/2004 | Lafontaine et al. |
| 6,835,203 B1 | | 12/2004 | Vardi et al. |
| 6,855,136 B2 | | 2/2005 | Dorros et al. |
| 6,932,829 B2 | | 8/2005 | Majercak |
| 6,945,977 B2 | | 9/2005 | Demarais et al. |
| 6,989,071 B2 | | 1/2006 | Kocur et al. |
| 7,037,320 B2 | | 5/2006 | Brady et al. |
| 7,131,981 B2 | | 11/2006 | Appling et al. |
| 7,144,364 B2 | | 12/2006 | Barbut et al. |
| 7,169,160 B1 | | 1/2007 | Middleman et al. |
| 7,306,617 B2 | | 12/2007 | Majercak |
| 7,396,358 B2 | | 7/2008 | Appling et al. |
| 7,485,139 B1 | | 2/2009 | Ciamacco, Jr. |
| 7,655,016 B2 | | 2/2010 | Demarais et al. |
| 7,691,081 B2 | | 4/2010 | Crossman |
| 7,758,626 B2 | | 7/2010 | Kim et al. |
| 7,771,401 B2 | | 8/2010 | Hekmat et al. |
| 7,842,056 B2 | | 11/2010 | Holman et al. |
| 7,846,175 B2 | | 12/2010 | Bonnette et al. |
| 7,922,687 B2 | | 4/2011 | Gingles |
| 7,927,363 B2 | | 4/2011 | Perouse |
| 7,959,584 B2 | * | 6/2011 | Esksuri .................. A61F 2/013 600/585 |
| 7,988,646 B2 | | 8/2011 | Taber |
| 8,062,258 B2 | | 11/2011 | Demarais et al. |
| 8,066,757 B2 | | 11/2011 | Ferrera et al. |
| 8,070,761 B2 | | 12/2011 | Weber et al. |
| 8,075,519 B2 | | 12/2011 | Min et al. |
| 8,100,935 B2 | | 1/2012 | Rosenbluth et al. |
| 8,118,827 B2 | | 2/2012 | Duerig et al. |
| 8,152,951 B2 | | 4/2012 | Zawacki et al. |
| 8,162,964 B2 | | 4/2012 | Piippo et al. |
| 8,167,821 B2 | * | 5/2012 | Sharrow ............ A61M 25/0108 600/433 |
| 8,556,926 B2 | | 10/2013 | Duerig et al. |
| 8,728,106 B2 | | 5/2014 | Weber et al. |
| 8,764,730 B2 | | 7/2014 | Taber |
| 8,777,977 B2 | | 7/2014 | Angel |
| 8,961,555 B2 | | 2/2015 | Duerig et al. |
| 8,968,350 B2 | | 3/2015 | Duerig et al. |
| 9,125,683 B2 | | 9/2015 | Farhangnia et al. |
| 9,126,016 B2 | | 9/2015 | Fulton |
| 9,126,020 B2 | | 9/2015 | Farhangnia et al. |
| 9,358,037 B2 | | 6/2016 | Farhangnia et al. |
| 9,364,255 B2 | | 6/2016 | Weber |
| 9,408,626 B2 | | 8/2016 | Tekulve |
| 2002/0010487 A1 | | 1/2002 | Evans et al. |
| 2002/0032391 A1 | | 3/2002 | McFann et al. |
| 2002/0116147 A1 | | 8/2002 | Vock et al. |
| 2002/0173816 A1 | | 11/2002 | Hung |
| 2003/0055445 A1 | | 3/2003 | Evans et al. |
| 2003/0078605 A1 | | 4/2003 | Bashiri et al. |
| 2003/0163082 A1 | | 8/2003 | Mertens |
| 2003/0171765 A1 | | 9/2003 | Kokate et al. |
| 2003/0171770 A1 | | 9/2003 | Kusleika et al. |
| 2003/0236533 A1 | | 12/2003 | Wilson et al. |
| 2003/0236564 A1 | | 12/2003 | Majercak |
| 2004/0064024 A1 | * | 4/2004 | Sommer ................ A61N 1/056 600/374 |
| 2004/0087971 A1 | | 5/2004 | Arnott |
| 2004/0158281 A1 | | 8/2004 | Boylan et al. |
| 2004/0204738 A1 | | 10/2004 | Weber et al. |
| 2004/0215220 A1 | | 10/2004 | Dolan et al. |
| 2004/0220473 A1 | | 11/2004 | Lualdi |
| 2005/0020974 A1 | | 1/2005 | Noriega et al. |
| 2005/0085846 A1 | | 4/2005 | Carrison et al. |
| 2005/0101938 A1 | | 5/2005 | Leiboff |
| 2005/0216044 A1 | | 9/2005 | Hong |
| 2006/0069323 A1 | | 3/2006 | Elkins et al. |
| 2006/0069421 A1 | | 3/2006 | Murray |
| 2006/0100544 A1 | * | 5/2006 | Ayala ................ A61M 25/0136 600/585 |
| 2006/0149129 A1 | | 7/2006 | Watts et al. |
| 2006/0155363 A1 | | 7/2006 | LaDuca et al. |
| 2006/0155366 A1 | | 7/2006 | LaDuca et al. |
| 2006/0190070 A1 | | 8/2006 | Dieck et al. |
| 2007/0010763 A1 | | 1/2007 | Lentz et al. |
| 2007/0083215 A1 | | 4/2007 | Hamer et al. |
| 2007/0123925 A1 | | 5/2007 | Benjamin et al. |
| 2007/0135826 A1 | | 6/2007 | Zaver et al. |
| 2007/0233220 A1 | | 10/2007 | Greenan |
| 2007/0250035 A1 | | 10/2007 | El-Nounou et al. |
| 2008/0027529 A1 | | 1/2008 | Hartley et al. |
| 2008/0058839 A1 | | 3/2008 | Nobles et al. |
| 2008/0097499 A1 | * | 4/2008 | Nash ............ A61B 17/320758 606/159 |
| 2008/0146967 A1 | * | 6/2008 | Richardson ............ A61L 31/10 600/585 |

(56) References Cited

U.S. PATENT DOCUMENTS

| | | | |
|---|---|---|---|
| 2008/0183103 A1 | 7/2008 | Blankenship et al. | |
| 2008/0249420 A1 | 10/2008 | Crossman | |
| 2008/0306468 A1 | 12/2008 | Tamai et al. | |
| 2009/0005754 A1* | 1/2009 | Soetermans | A61M 25/0169 604/500 |
| 2009/0005757 A1 | 1/2009 | Taber | |
| 2009/0048577 A1 | 2/2009 | Gillies et al. | |
| 2009/0048654 A1 | 2/2009 | Chmura et al. | |
| 2009/0062840 A1 | 3/2009 | Angel | |
| 2009/0105642 A1 | 4/2009 | Leonard et al. | |
| 2009/0105644 A1 | 4/2009 | Leonard et al. | |
| 2009/0105724 A1* | 4/2009 | Yoshizaki | A61M 25/0041 606/129 |
| 2009/0163846 A1 | 6/2009 | Aklog et al. | |
| 2009/0292307 A1 | 11/2009 | Razack | |
| 2010/0019189 A1* | 1/2010 | Kurita | A61B 5/06 252/62.54 |
| 2010/0069880 A1* | 3/2010 | Grayzel | A61M 25/09 604/509 |
| 2010/0114113 A1 | 5/2010 | Dubrul et al. | |
| 2010/0204712 A1 | 8/2010 | Mallaby | |
| 2010/0280450 A1 | 11/2010 | Jain | |
| 2010/0286465 A1 | 11/2010 | Benson | |
| 2010/0292614 A1 | 11/2010 | Delaney | |
| 2010/0331951 A1 | 12/2010 | Bei et al. | |
| 2011/0022038 A1 | 1/2011 | Seshadri et al. | |
| 2011/0137163 A1 | 6/2011 | Eder | |
| 2011/0160763 A1 | 6/2011 | Ferrera et al. | |
| 2011/0208222 A1 | 8/2011 | Ljahnicky et al. | |
| 2011/0218503 A1* | 9/2011 | Kaveckis | A61M 25/00 604/284 |
| 2011/0251591 A1 | 10/2011 | Taber | |
| 2011/0295234 A1 | 12/2011 | Eaton | |
| 2012/0022579 A1 | 1/2012 | Fulton | |
| 2012/0046730 A1 | 2/2012 | von Oepen et al. | |
| 2012/0101561 A1 | 4/2012 | Porter | |
| 2012/0184952 A1* | 7/2012 | Jenson | A61B 18/1492 606/41 |
| 2012/0197277 A1 | 8/2012 | Stinis | |
| 2012/0239064 A1 | 9/2012 | Cartier et al. | |
| 2012/0259314 A1 | 10/2012 | Guo et al. | |
| 2012/0316600 A1 | 12/2012 | Ferrera et al. | |
| 2013/0253474 A1 | 9/2013 | Farhangnia et al. | |
| 2014/0025004 A1* | 1/2014 | Falk | A61M 25/0105 604/96.01 |
| 2014/0031855 A1 | 1/2014 | Clubb et al. | |
| 2014/0128844 A1 | 5/2014 | Komowski et al. | |
| 2014/0142505 A1* | 5/2014 | Lin | A61M 25/1029 604/103.06 |
| 2014/0207179 A1 | 7/2014 | Farhangnia et al. | |
| 2014/0249511 A1 | 9/2014 | Taber | |
| 2014/0257248 A1* | 9/2014 | Millett | A61M 25/09041 604/528 |
| 2014/0257352 A1 | 9/2014 | Weber et al. | |
| 2014/0277008 A1 | 9/2014 | Farhangnia et al. | |
| 2014/0277015 A1 | 9/2014 | Stinis | |
| 2014/0288583 A1 | 9/2014 | Stinis | |
| 2015/0025555 A1 | 1/2015 | Sos | |
| 2015/0073538 A1 | 3/2015 | Thomas et al. | |
| 2015/0126967 A1 | 5/2015 | Taber | |
| 2015/0157215 A1 | 6/2015 | Stigall | |
| 2015/0157216 A1 | 6/2015 | Stigall et al. | |
| 2015/0250991 A1 | 9/2015 | Silvestro | |
| 2015/0297250 A1 | 10/2015 | Farhat et al. | |
| 2015/0313479 A1 | 11/2015 | Stigall et al. | |
| 2015/0328433 A1 | 11/2015 | Farhangnia et al. | |
| 2015/0335345 A1 | 11/2015 | Farhangnia et al. | |
| 2015/0343178 A1 | 12/2015 | Fulton, III | |
| 2016/0008584 A1* | 1/2016 | Root | A61M 25/09 604/510 |
| 2016/0015935 A1* | 1/2016 | Chan | A61M 25/0105 604/510 |
| 2016/0022293 A1 | 1/2016 | Dubrul et al. | |
| 2016/0066936 A1 | 3/2016 | Weber et al. | |
| 2016/0120566 A9 | 5/2016 | Farhangnia et al. | |
| 2016/0235429 A1 | 8/2016 | Farhangnia et al. | |

FOREIGN PATENT DOCUMENTS

| | | |
|---|---|---|
| EP | 0592726 A1 | 4/1994 |
| EP | 0829271 A2 | 3/1998 |
| EP | 1025813 A2 | 8/2000 |
| EP | 1225949 A1 | 7/2002 |
| EP | 1237488 A1 | 9/2002 |
| EP | 1365830 A1 | 12/2003 |
| EP | 1534181 A2 | 6/2005 |
| EP | 1610718 A2 | 1/2006 |
| EP | 1637084 A1 | 3/2006 |
| EP | 1642539 A1 | 4/2006 |
| EP | 1699518 A1 | 9/2006 |
| EP | 1970093 A1 | 9/2008 |
| EP | 1496972 A2 | 11/2008 |
| EP | 2203209 A1 | 7/2010 |
| EP | 2262567 A1 | 12/2010 |
| EP | 2670318 A1 | 12/2013 |
| EP | 2714172 A1 | 4/2014 |
| EP | 2908783 A1 | 8/2015 |
| EP | 2977072 A1 | 1/2016 |
| EP | 3043747 A1 | 7/2016 |
| EP | 3043748 A1 | 7/2016 |
| EP | 3122412 A1 | 2/2017 |
| GB | 2472213 A | 2/2011 |
| JP | 2002/537943 A | 11/2002 |
| JP | 2015-131117 A | 7/2015 |
| WO | 95/10317 | 4/1995 |
| WO | WO99/48549 | 9/1999 |
| WO | 2000/053120 A1 | 9/2000 |
| WO | 2002/67772 A2 | 9/2002 |
| WO | 2004/026180 A2 | 4/2004 |
| WO | 2007/062879 A1 | 6/2007 |
| WO | 2008/051898 A2 | 5/2008 |
| WO | 2009/003113 A1 | 12/2008 |
| WO | 2010/102307 A1 | 9/2010 |
| WO | 2011/119879 A1 | 9/2011 |
| WO | 2012/160562 A1 | 11/2012 |
| WO | 2014/066412 A1 | 5/2014 |
| WO | 2015/148364 A1 | 10/2015 |
| WO | 2017/053798 A1 | 3/2017 |

OTHER PUBLICATIONS

Extended European Search Report dated Dec. 4, 2015 in related European Application No. 15181301.1.

PCT/US08/68380: International Search Report dated Oct. 2, 2008.

PCT/US13/66217: International Preliminary Report on Patentability dated Sep. 16, 2014.

PCT/US13/66217: International Search Report and Written Opinion dated Jan. 16, 2014.

PCT/US15/021975: International Search Report and Written Opinion dated Jun. 26, 2015.

U.S. Appl. No. 61/064,715, filed Mar. 21, 2008, Taber.

U.S. Appl. No. 60/929,395, filed Jun. 26, 2007, Taber.

U.S. Appl. No. 60/960,900, filed Oct. 19, 2007, Taber.

U.S. Appl. No. 60/996,057, filed Oct. 26, 2007, Taber.

Extended European Search Report dated May 3, 2016 in related European Application No. 13848899.4.

PCT/US16/53442: International Search Report and Written Opinion dated Feb. 16, 2017.

U.S. Appl. No. 14/119,873: Non-Final Office Action dated Sep. 16, 2015.

* cited by examiner

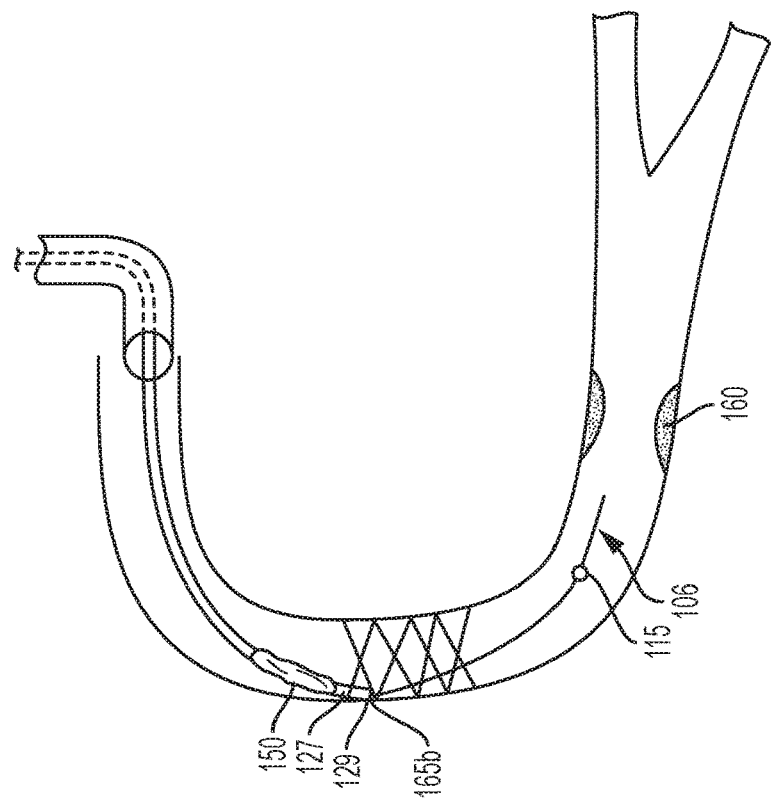
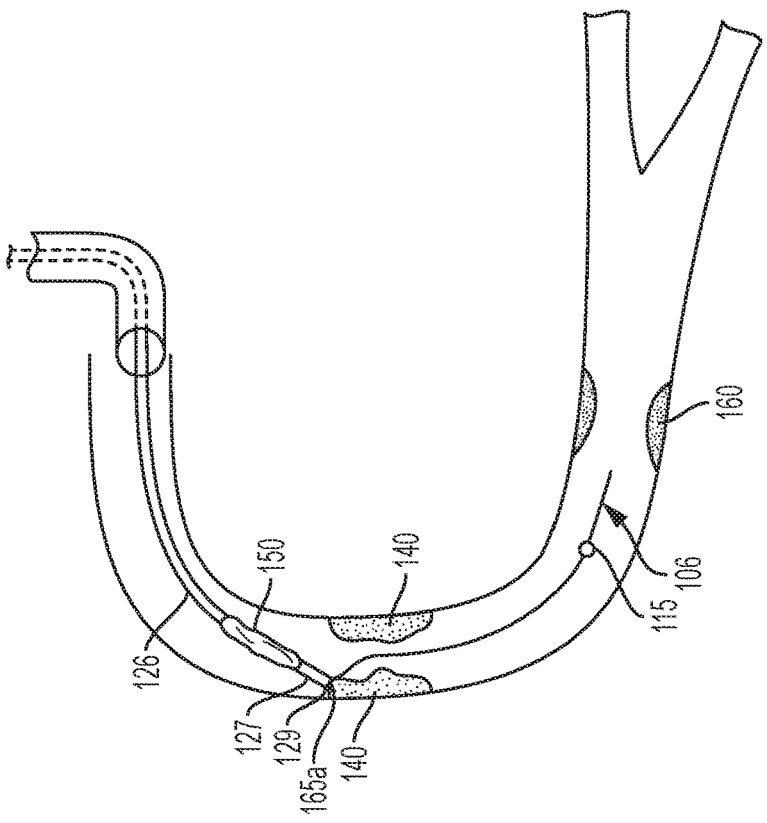

GUIDE WIRES, CATHETERS, AND GUIDE WIRE CATHETER SYSTEMS AND METHODS

CROSS-REFERENCE TO RELATED APPLICATIONS

This application claims priority to U.S. Patent Application No. 62/232,829 filed on Sep. 25, 2015, and 62/359,090 filed on Jul. 6, 2016, which are hereby incorporated herein by reference in their entireties.

TECHNICAL FIELD

The present invention relates to guide wires, catheters, and guide wire catheter systems and methods.

BACKGROUND

Advancing catheter devices such as balloons or stents over guide wires through the vasculature can be impaired by vessel tortuosity, plaque, calcification or previously deployed devices, such as stents. This resistance to advancement can result in the inability to move or place the device within the vasculature to the desired location.

What is needed are guide wires, catheters and guide wire systems and methods for improved advancement to desired locations within vasculatures.

BRIEF SUMMARY OF THE INVENTION

Various features and embodiments of guide wires, catheters, and guide wire catheter systems and methods are contemplated.

A guide wire, can include: an elongated member having a proximal end and a distal end; and an enlargement being disposed on the distal end of the elongated member, the enlargement being spaced proximally from a distal tip of the distal end of the elongated member. The proximal end of the elongated member can have a difference in structure between the distal end of the elongated member.

A portion of the proximal end of the elongated member can have a rigidity coefficient greater than a portion of the distal end. The guide wire can further include a bend in the elongated member, the bend being disposed proximate the enlargement on a proximal side of the enlargement.

At least one of the bend and the enlargement can have a hydrophilic coating or can be radio-opaque.

The bend can be at least one of: a curve, a sinusoidal curve, a non-linear section, an angulation, a peak, a valley, a squiggle, curvilinear, and helical. The bend can have a variable stiffness. The bend can have a stiffness coefficient greater than the remaining portion of the elongated member.

The enlargement can have a profile that is determined based upon a catheter tip profile and the enlargement profile can be greater than the catheter tip profile. The enlargement profile can be about 30 percent larger than the catheter tip profile.

A diameter of the guide wire can be 0.014 inches and a diameter of the enlargement can be 0.027 inches, when used with a 0.021 inch diameter catheter tip.

The guide wire can further include linearly spaced radio-opaque markers to facilitate measurement of a lesion length.

The enlargement can have a radial dimension that is determined based upon a catheter tip outer diameter. The enlargement can be proximally offset from a distal tip of the distal end of the guide wire.

The enlargement can be spherical shaped. The enlargement can be non-spherical shaped.

A method of navigating through vasculature, can include: advancing a guide wire through a vessel, the guide wire having a substantially uniform outer diameter, and the guide wire having a distal portion that includes a radial bulge; and advancing a catheter over the guide wire, the catheter having a proximal end and a distal end; encountering an obstruction hindering advancement of the catheter; and withdrawing the guide wire through the catheter to position the radial bulge in contact with the distal end of the catheter, wherein the step of withdrawing can allow the distal end of the catheter to be displaced away from the obstruction to allow advancement of the catheter.

The method can also include advancing the catheter in contact with the radial bulge together past the obstruction based on the guide wire displacing the distal end of the catheter.

The method can also include advancing the guide wire and the catheter separately past the obstruction. The method can also include the step of: maintaining the distal end of the catheter at the obstruction while the guide wire is withdrawn and until the radial bulge is in contact with the distal end of the catheter.

The step of withdrawing can further include withdrawing a radial bulge that is larger than the distal end of the catheter causing the distal end of the catheter to become unobstructed.

The step of advancing a guide wire can further include advancing the guide wire with a curve proximate and proximal to the radial bulge. The method can further include rotating the guide wire upon encountering the obstruction to assist in passage past or penetration through the obstruction of the guide wire and catheter.

A catheter guide wire system, can include: the guide wire as described above; and a catheter having a shaft and being configured to encompass the guide wire, the catheter having a proximal portion and a distal portion.

The guide wire of the catheter guide wire system can include linearly spaced radio-opaque markers to facilitate measurement of a lesion length.

A tip of the distal end of the guide wire of the catheter guide wire system can have a same outer diameter as the uniform outer diameter of the guide wire.

The enlargement can be proximally offset from a distal tip of the distal end of the guide wire.

The distal portion can be enlarged in relation to the catheter shaft, the tip of the distal portion being configured to engage with the enlargement of the guide wire upon the catheter becoming stuck.

The tip of the distal portion of the catheter can be bulb-shaped. An outer diameter of the tip of the distal portion of the catheter can be 30% greater than an outer diameter of the shaft of the catheter. The catheter can include a balloon that protrudes radially from, and can extend along, the shaft of the catheter.

The enlargement of the system can be spherical shaped. The enlargement of the system can be non-spherical shaped.

The guide wire of the system can have a non-linear portion of at least one of: a curve, a sinusoidal curve, a non-linear section, an angulation, a peak, a valley, a squiggle, curvilinear, and helical.

The non-linear section of the system can be adjacent to the enlargement. The non-linear section of the system can be proximal to the enlargement.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

Various representative embodiments of guide wires, catheters, and guide wire catheter systems and methods in accordance with the principles of the invention are shown in the pages of drawings provided herein.

FIG. 5A illustrates an integrated catheter-guide wire system or catheter tracking over a guide wire encountering an obstruction in a vasculature, according to an embodiment of the invention.

FIG. 5B illustrates a guide wire system stuck on a stent in a vasculature, according to an embodiment of the invention.

DETAILED DESCRIPTION OF THE INVENTION

Figure 1:
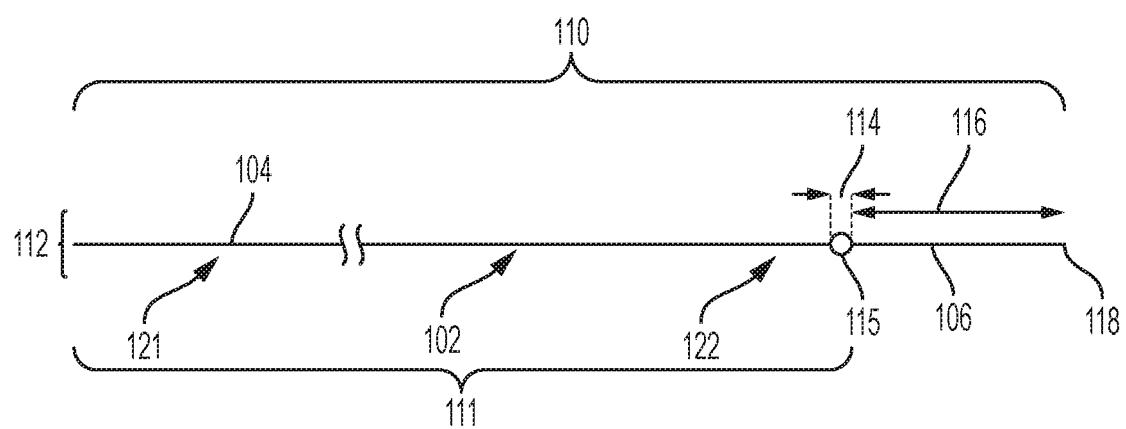
FIG. 1 illustrates a guide wire with an enlargement, according to an embodiment of the invention.

Some embodiments of the current invention are discussed in detail below. In describing embodiments, specific terminology is employed for the sake of clarity. However, the invention is not intended to be limited to the specific terminology and examples selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

The invention is generally directed to a guide wire configuration and related methods of using the guide wire. Additionally, the invention is directed to a catheter with a configured distal end and/or tip and methods of using the same with a conventional guide wire and/or a guide wire configured in accordance with the principles of embodiments of the invention. The guide wire and/or catheter can be configured to effectively, efficiently and/or reliably advance catheter devices such as balloons or stents through the vasculature and, more particularly, over guide wires through the vasculature.

The vasculature can be the type of vasculature that has tortuosity, plaque, calcification, previously deployed stents, or other blockages that make it difficult to traverse a catheter through the vasculature. The guide wire and/or catheter can be configured in accordance with the principles of embodiments of the invention to improve and/or achieve advancement through the vasculature. Moreover, the methods of using the configured guide wire and/or the configured catheter with a conventional guide wire and/or a configured guide wire in accordance with the principles of embodiments of the invention can be used to improve and/or achieve advancement through the vasculature.

In certain embodiments, the guide wire is configured so that it can engage a catheter tip and cause the catheter tip to deflect and/or shift so that the catheter can pull away from the obstruction and/or vasculature and/or it can allow the catheter tip to advance over and/or beyond the resistance as a result of the guide wire configurations. Alone and/or in combination with each other, the systems and methods in accordance with the principles of embodiments of the invention can more reliably advance and/or become freed from an obstruction/resistance for further advancement.

By configuring a guide wire that can be conventionally placed in the vasculature prior to an interventional procedure, such as stenting and/or balloon angioplasty, when resistance is encountered the entire system does not need to be removed and/or the catheter/device tracking over the guide wire does not need to be removed. Rather the guide wire, already in position distally, can be pulled back or retracted into the catheter/device, in accordance with the principles of embodiments of the invention. The configuration of the guide wire and/or the configuration of an enlargement on the guide wire can be pulled back into contact with the distal catheter tip, but can be configured to prevent complete withdrawal of the guide wire. The configuration of the guide wire can prevent the guide wire from full withdrawal through the catheter. The guide wire configuration can act as a stopper or impediment controlling the extent of entry into the catheter tip and how the catheter tip interacts and reacts to the guide wire configuration engagement with and/or into the catheter tip. In accordance with the principles of embodiments of the invention, in an alternate embodiment the guide wire can be removable. In one embodiment, the guide wire configuration can provide for temporary removal prevention, but have the ability under certain conditions to be retractable through the catheter. In another embodiment, the guide wire configuration, in particular the enlargement, could be compressible or collapsible allowing it to be removed.

The guide wire configuration, during and upon retraction, can interact cooperatively with the distal tip of the catheter allowing the catheter/device to successfully pass the resistance or obstruction. The interaction and arrangement between the catheter tip and guide wire configuration can occur over a length of the configuration and also the breadth and/or width dimension of the guide wire configuration. In one aspect of the configuration of the guide wire, the catheter tip can be shifted or deflected by the configuration. In another aspect, the configuration of the guide wire can blunt and/or modify the distal catheter tip for reduced resistance and/or resistance free advancement. In one aspect this preferably can be accomplished by a configuration that can be rounded and/or curved and/or that does not create edges or focal points that can create new resistance. In another aspect, when the configuration can be proximate and/or engaged with the catheter tip, the now-leading end of the combination can be the lead/leading end of the guide wire configuration that can be more particularly adapted in combination with the catheter/device to advance through or beyond the obstructions and/or resistance. For example, the curved leading end of the enlargement can readily move over the resistance or obstruction more effectively than the leading edge of the catheter. In one aspect the guide wire configuration and the catheter distal tip can be in contact, held and/or compressed together, allowing the combination to advance past the resistance/obstruction. In effect, the catheter can include a temporarily and reversibly modified tip in-situ for advancement beyond resistance and/or obstructions. Once the resistance or obstruction can be bypassed, the guide wire can return to its distal positioning for tracking the device over the guide wire in normal course allowing devices to treat distally from the resistance and/or obstruction where the devices could not have otherwise accessed interventionally without the use of the invention. The guide wire configuration and method of use can be repeatable and can be used one or more times throughout a procedure and one or more locations in the vasculature and with one or more devices tracking over the guide wire.

Figure 2:
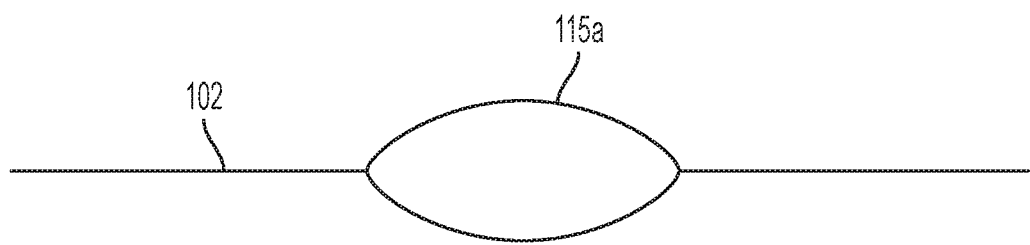
FIG. 2 illustrates a guide wire with an alternate enlargement, according to an embodiment of the invention.
Figure 3:
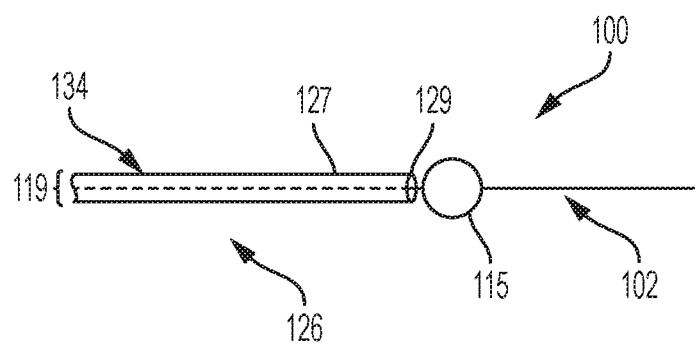
FIG. 3 illustrates a guide wire system, according to an embodiment of the invention.

Referring to the figures, various aspects of the inventions are shown. Referring to FIGS. 1-3, a guide wire configuration of the type having an enlargement is shown in FIG. 1, and another enlargement configuration is shown in FIG. 2. While the guide wire with the enlargement of FIG. 1 is shown in combination with a catheter where the catheter tip is proximate the guide wire enlargement and shows the relative dimensions and geometry of an exemplary configuration for purposes of modifying a catheter tip in-situ and/or enabling the otherwise unpassable and/or snagged catheter tip to advance. The enlargement can have a dimension selected based upon a lumen diameter of a distal tip of the device, such as, the catheter lumen or inner diameter. The enlargement can have a dimension larger than the catheter lumen dimension, such as, the catheter lumen inner diameter. As shown in FIG. 1, a guide wire 102 can include an elongated member having a proximal portion 121 and a distal portion 122. The guide wire 102 can have an enlargement 115 disposed at the distal end 122 of the elongated member. The enlargement can be spaced proximally from a distal tip 118 of the guide wire 102. The guide wire enlargement, as shown, can be larger than the catheter tip outer diameter (OD). The size and the OD of the enlargement can vary in accordance with the principles of embodiments of the invention. The same and/or alternate sizes, geometries and/or configurations are contemplated, including, for use with a catheter of the type where the catheter tip is already designed with an enlargement (i.e., bulbous), as explained with reference to FIG. 29.

The guide wire 102 can have a unique geometry with a focal enlargement in the guide wire diameter 112 at a distance "116" from the distal tip 118 of the guide wire 102. The enlargement 115 can have a spherical shape or a sphere or globe-shape, as shown in FIG. 1. In another embodiment, as shown in FIG. 2, the enlargement 115a can be the shape as shown, such as an elongate sphere. Various shapes and/or geometries can be contemplated including prolate, egg-shaped, elongated shapes, spherical or otherwise non-spherical in accordance with the principles of embodiments of the invention. The enlargement is not limited to these shapes of FIGS. 1 and 2. Various shapes are contemplated in accordance with the principles of embodiments of the invention. The enlargement can be shaped, sized and/or configured such that it can engage and/or abut a catheter tip, in whole or in part, yet preferably cannot allow the guide wire, as a result of at least part of the configuration, to be fully withdrawn through a lumen of the catheter under normal conditions in the setting and context of an interventional procedure, for example. The alternate enlargement 115*a* configuration as shown in FIG. 2 can be contemplated, as well as other configurations. As shown in FIG. 2, the shape can have a curved outer surface in the form of a symmetrical pod-shaped volume of material. The enlargements can be solid and/or hollow and made of conventional guide wire materials. By having curved and/or non-linear surfaces on the enlargement, either in whole or in part, there can be smooth and/or less resistance when engaging a target region such as the vasculature and/or previously implanted devices. Sharp and/or acute linear angles alone can have a tendency to get caught similar to the distal tip of the catheter.

Various distances and lengths are also contemplated in accordance with the principles of embodiments of the invention. The guide wire 102 can have a length represented by 110. An elongated member 104 can have a uniform outer diameter 112 and a length represented by 111. The enlargement 115 can have a dimension, such as a diameter, as shown, represented by 114. The guide wire 102 can include a distal portion 106 that has an outer diameter that is smaller than the outer diameter of the elongated member 104. The distal portion 106 can be a distance of about 3 cm.

A portion of the proximal portion 121 of the elongated member can have a rigidity coefficient greater than a portion of the distal portion 106 of the elongated member. In an embodiment, the proximal portion 121 of the guide wire 110 has a mandrel or mandrel backbone while the distal portion 106 does not have a mandrel, which allows for the proximal portion 121 to have a larger diameter than the distal portion 106. The mandrel can be disposed inside at least a portion of the proximal portion 121 of the elongated member that provides the greater rigidity coefficient to the proximal portion. The rigidity and/or flexibility of the guide wire 102 can vary along its length to achieve the principles of embodiments of the invention. The distal portion 106 can be made rigid in whole or in part as well as the enlargement 115. The rigidity of the enlargement and/or the guide wire as it relates to the principles of embodiments of the invention can be relative to the catheter being use and the ability of the guide wire configuration to allow the catheter tip to become freed or overcome resistance and/or prevent the guide wire from completely passing through the catheter. In one aspect of the invention this can be accomplished by way of the guide wire configuration alone and/or in combination with the materials used as would be understood by one skilled in the art.

The enlargement 115 or 115*a* can have a profile that is determined based upon a distal tip 129 profile, as shown in FIG. 3. A profile of the enlargement 115 can be greater than a profile of the distal tip 129. In an embodiment, an outer diameter of the enlargement can be greater than the inner diameter of the catheter distal tip 129 such that the enlargement 115 of the guide wire 102 cannot retreat inside the catheter. Partial retreat of the guide wire 102 can be contemplated, however, preferably, complete withdrawal/removal during the intended use in conjunction with the catheter 126 can be avoided. An outer diameter of the enlargement 115 can be greater than an inner diameter of the catheter distal tip 129. For example, the enlargement profile can be about 30 percent larger than the catheter tip profile. The enlargement 115 can have a radial dimension that is determined based upon an outer diameter 119 of the distal tip 129 of the catheter 126. In other embodiments, one or more, but not necessarily all, enlargements can be configured to retreat inside at least a portion of the catheter 126. In an embodiment, the catheter tip can be about 2-3 mm long.

Thus, embodiments of the invention can include a catheter used in conjunction with the guide wire. As shown in FIG. 3, a guide wire system 100 can include a guide wire 102 and a catheter 126 having a shaft that is configured to encompass the guide wire 102. The catheter 126 can have a proximal portion 134 and a distal portion 127. In the guide wire system 100, the guide wire 102 can have an enlargement 115 disposed at the distal end 122 of the elongated member. A distal tip 129 of the catheter 126 can be configured to abut and/or contact the enlargement 115 of the guide wire in a closed position and/or a pulled back position.

The guide wire system 100 can include variations of the guide wire 102 as heretofore disclosed and/or variations to the guide wire disclosed hereafter.

Referring to FIGS. 1 and 3 in combination, a diameter 112 of the guide wire can be about 0.014 inches and a diameter 114 of the enlargement can be about 0.027 inches, when used with a 0.021 inch diameter 119 catheter tip 129 approximately 30% larger than catheter tip outer diameter. Various other percentages are contemplated in accordance with the principles of embodiments of the invention.

Figure 4:
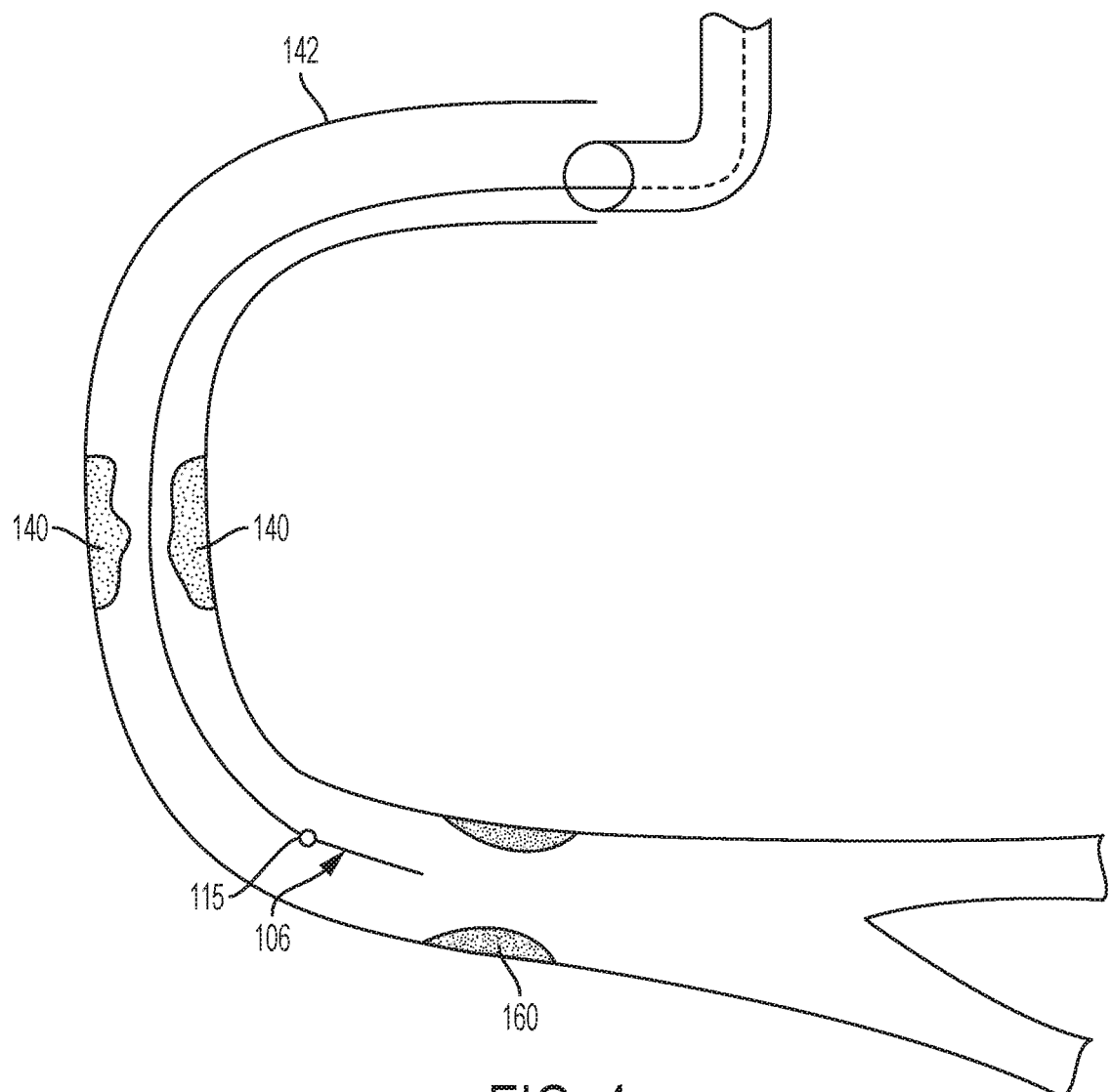
FIG. 4 illustrates a guide wire in a vasculature, according to an embodiment of the invention.

Another aspect of the invention relates to the methods of using the guide wire 102. FIGS. 4-9 illustrate methods of using the guide wire 102. As shown in FIG. 4, a guide wire system can be used in a method of navigating through vasculature. This method can include advancing the guide wire 102 through a vessel 142. A guide wire 102 can be first advanced into the vasculature, distal to the region of a blockage or resistance. The vessel 142 can include any vasculature such as a blood vessel. The guide wire 102 can have a substantially uniform outer diameter, and the guide wire can have a distal portion that includes an enlargement or radial bulge 115.

In the system 100, the guide wire 102 can include linearly spaced radio-opaque markers to facilitate measurement of a lesion length. In the system 100, a tip of the distal portion 106 of the guide wire 102 can have a same outer diameter as the uniform outer diameter of the guide wire and/or a conventional guide wire distal end for navigating the vasculature. In the system 100, the enlargement 115 can be proximally offset and/or spaced from a distal tip of the distal end of the guide wire. The enlargement 115 as shown can be a generally spherical shape. The enlargement can be spherical-shaped, non-spherical shaped and/or other configurations.

The catheter can include any catheter and/or medical device. The catheter can include a balloon catheter, including a deflated or shrunken balloon 150 that can be expandable to protrude radially from, and extend along, the shaft of the catheter. A stent can be included.

FIG. 5A shows a system in the vasculature of the type having plaque, calcification and/or an occlusion. FIG. 5B shows a system in the vasculature of the type having a previously deployed stent implanted in the vasculature.

As shown in FIG. 5A, the method can include advancing the catheter 126 over the guide wire 102. The catheter can have a distal tip 129 that is configured to interface with the guide wire 102. FIG. 5A shows the guide wire system encountering an obstruction 140 that hinders advancement of the catheter 126. In an embodiment, the encountering the obstruction is intended to be interpreted broadly as, for example, the catheter tip being prevented by any condition in the vessel from advancing down the vessel.

For example, the encountering the obstruction can include getting snagged on an obstruction 140, or meeting an obstruction 140 with the tip of the catheter head-on or in the direction of the vessel abutting the obstruction such that the tip of the catheter cannot advance down the vessel. This can take place at a stuck position 165 as shown in FIG. 5A. FIG. 5B is another illustration of the guide wire system encountering an obstruction or blockage 140, in this case, a previously placed stent. The catheter tip can get caught at the edge immediately following a tight corner because the catheter has been advancing in a straight path. Thus, the catheter tip can become obstructed by the physical resistance created by the stent. Also, catheter-guide wire systems can have an unsmooth transition point between the tip of the catheter (having an outer diameter of e.g., 0.021 inch diameter) and the guide wire (having e.g., 0.014 inch diameter). The unsmooth transition point can be a result of changing rigidity coefficients between the catheter and the guide wire, as well as a physical lip created by the step down in diameter. The enlargement as described herein can address this and allow for this unsmooth transition point or catheter tip to not get hung up in the vessel wall resistance in the first place or to be freed if resistance is encountered. That is, when the catheter tip is in contact with the enlargement 115, for example at a stuck position 165, the tip of the catheter is biased against the wall of the vessel due to the size and shape of the enlargement 115. This favorable alignment can be beneficial and can avoid allowing the physical transition point/tip of the catheter to abut the vessel wall causing resistance.

Figure 6B:
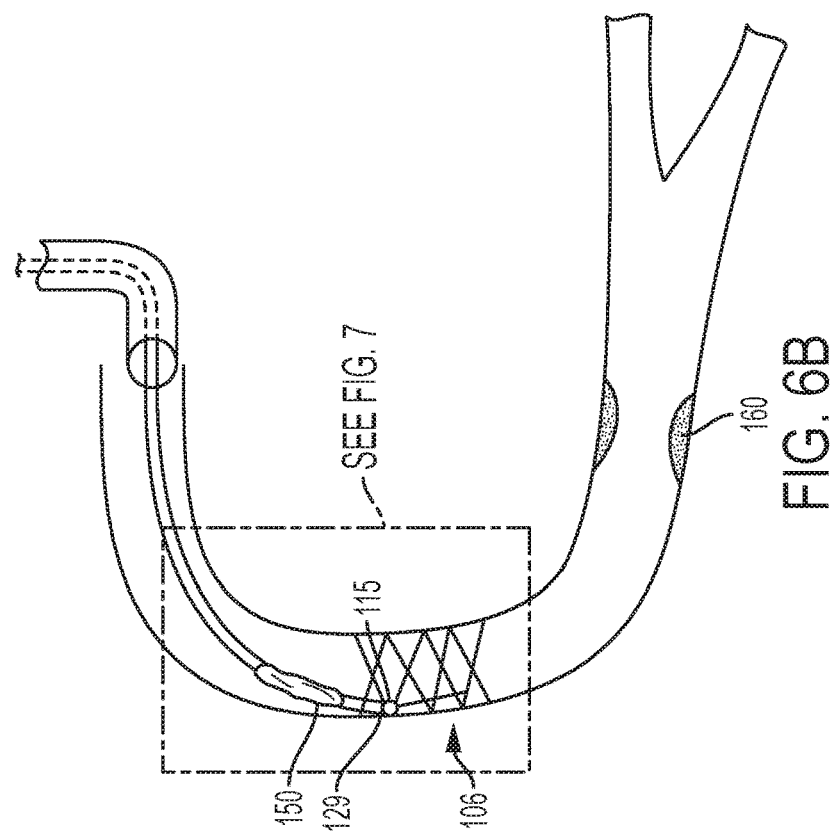
FIG. 6B illustrates a guide wire-catheter system with the catheter tip being lifted off the vessel wall by the guide wire enlargement, freeing the device from the stent to advance, according to an embodiment of the invention.
Figure 6A:
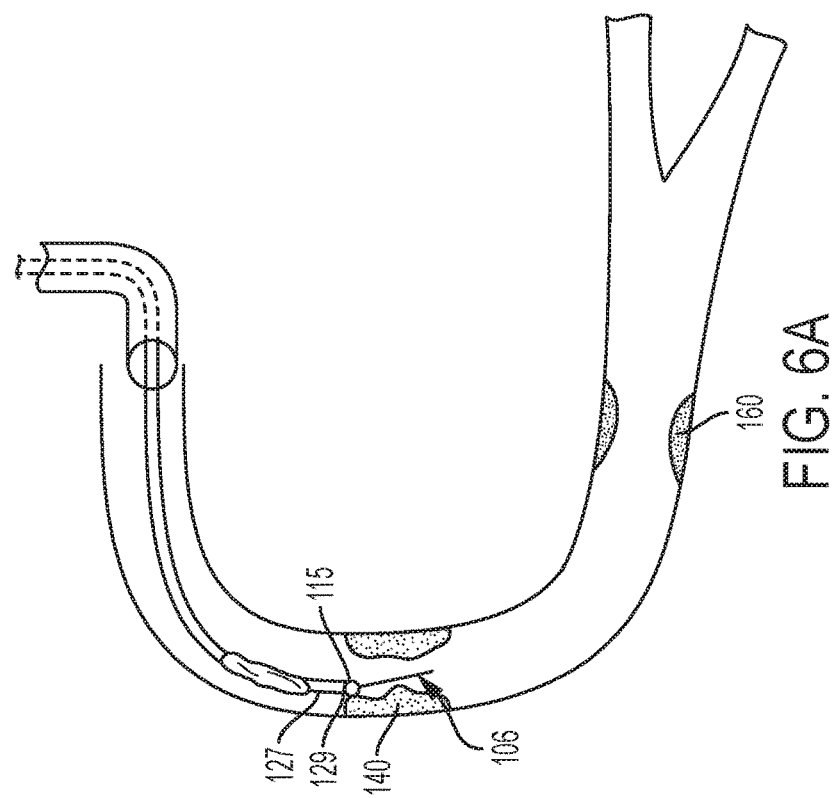
FIG. 6A illustrates a guide wire-catheter system with the catheter tip being lifted off the vessel wall by the guide wire enlargement, freeing the device from the obstruction to advance, according to an embodiment of the invention.

FIGS. 6A and 6B show that upon encountering the obstruction 140, the guide wire 102 can be retracted through the catheter 126 to position the enlargement 115 near or at a distal tip 129 of the catheter 126. Retracting the guide wire 102 can include having the catheter remain stationary while the guide wire 102 retracts. In some embodiments, the catheter 126 can also retract, but at a slower rate than the guide wire is retracted such that an enlargement of the guide wire meets up with the catheter 126. The enlargement in accordance with the principles of embodiments of the invention can pull, push, and/or move the catheter from off and/or away from the obstruction. Indeed, the leading end of the enlargement can take over navigation. The enlargement can create a tip that can pass through more reliably and not catch or hook on the vasculature or implanted stent, for example.

As shown in FIGS. 6A and 6B, the step of retracting can allow the distal tip 129 of the catheter 126 to be displaced away from the obstruction 140 to allow advancement of the catheter 126. The guide wire 102 can be advanced distal to the point of resistance. As resistance is encountered in advancing the catheter device over the guide wire 102, the guide wire 102 can be retracted or pulled back to the tip of the catheter.

Figure 7:
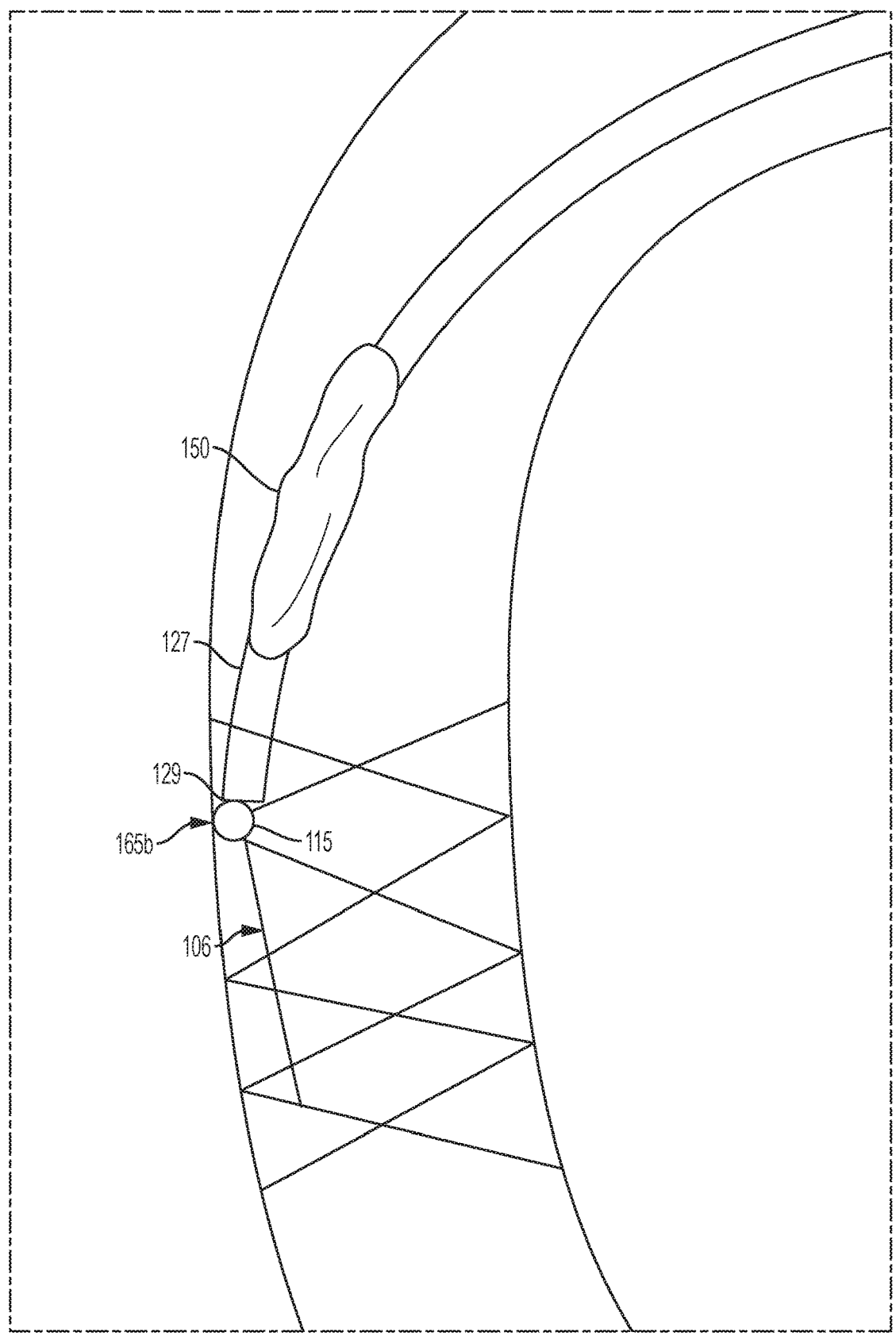
FIG. 7 shows a zoomed-in view of FIG. 6B, according to an embodiment of the invention.

FIG. 7 shows a zoomed-in view of FIG. 6B of the enlargement 115 interfacing with the distal tip 129 such that it lifts the tip away from the vessel wall obstruction, i.e., stuck position 165. As can be seen, the distal tip 129 is dislodged from the embedded position 165 of the stent in part due to the enlargement 115 interfacing with the distal tip 129. The combination can be advanced together to pass resistance with the enlargement leading. After the catheter has been dislodged and/or free to move again, the guide wire can be returned to its distal position to allow the catheter to track traditionally again. The configuration, size, shape and/or geometry of the enlargement can varied in accordance with the principles of embodiments of the invention so long as it can assist in lifting the catheter tip off of and away from the resistance without creating further problems such as bends or kinks. For example, a cone-shape enlargement with the peak of the cone pointing distally may not be able to lift-off of the resistance and instead the point of the cone may create further resistance.

Figure 8:
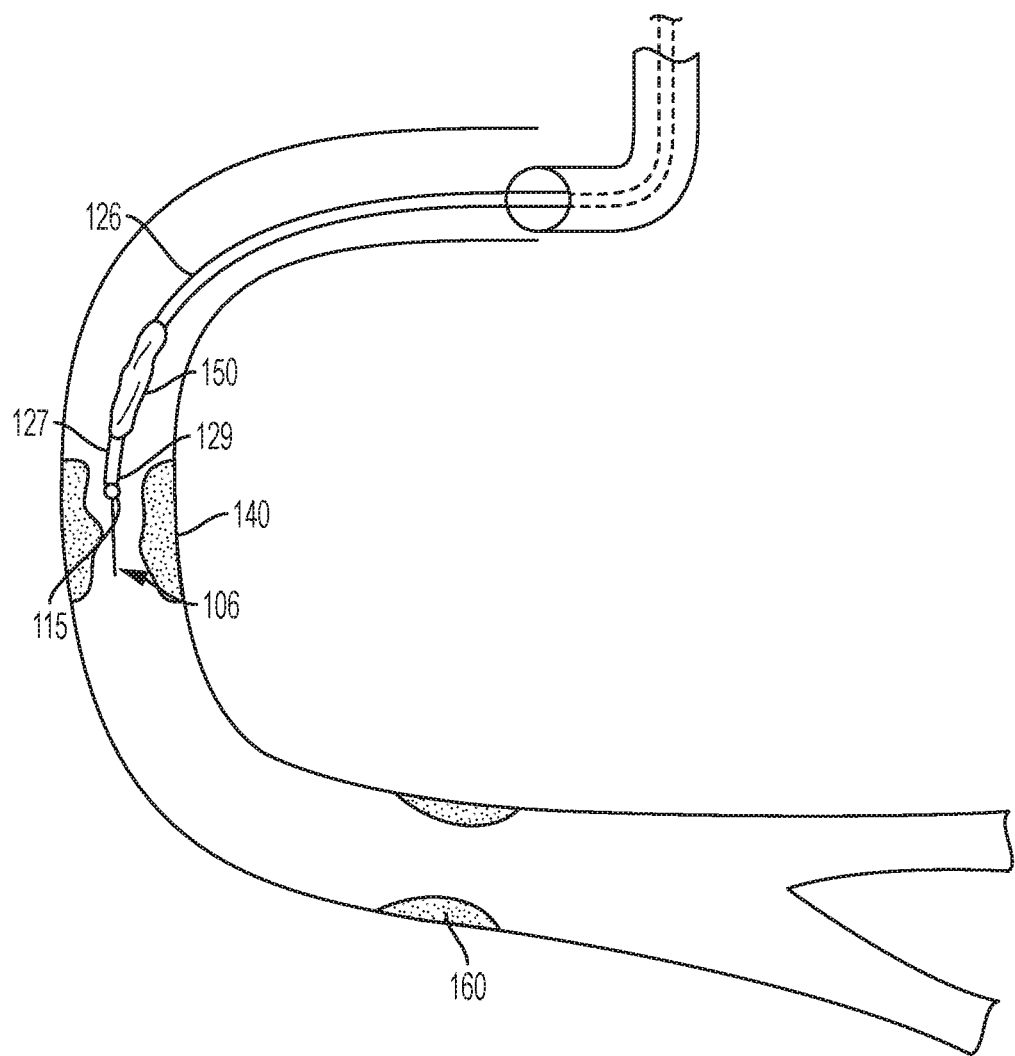
FIG. 8 illustrates a freed catheter-guide wire system after positioning the enlargement at the tip of the catheter, overcoming the vessel wall resistance of FIG. 5A according to an embodiment of the invention.

As shown in FIG. 8, the guide wire system 100 can be retracted with an enlargement 115 causing the distal end 127 of the catheter to become centrally aligned within the vessel and/or unobstructed. The unique configuration and/or geometry of the guide wire can lift the catheter tip away from the obstruction 140. In one aspect, the unique geometry of the guide wire 102, for example, the enlargement, can lift a tip 129 of the catheter 126 away from the resistance.

Alternatively, instead of centrally aligning the projection of the system, the enlargement can lead the guide wire system as a unit through the blockage. That is, once the guide wire has been retracted to interface the enlargement with the distal tip of the catheter or the guide wire system otherwise freed from the blockage, the configuration, such as, the substantially round profile of the enlargement can have an ability to minimize the likelihood of getting stuck on blockages due to the round nature of the surface of the enlargement and/or the relative size and dimensions of the enlargement and the catheter tip. After passing through one or more blockages, the tip of the guide wire can proceed ahead of the tip of the catheter.

Figure 9A:
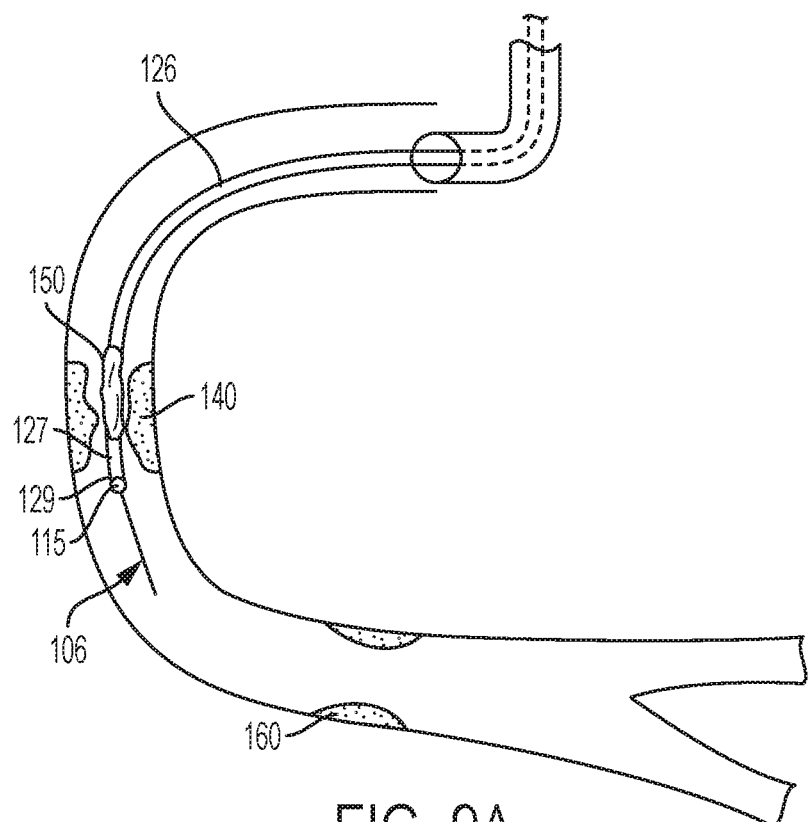
FIG. 9A illustrates a guide wire system as in FIG. 8 traversing more distally past vessel wall resistance, according to an embodiment of the invention.

FIG. 9A shows that the catheter 126 and enlargement 115 can then be advanced as a unit forward, past the point of resistance. The method can include advancing the guide wire and the catheter separately past the obstruction. The method can include maintaining the distal end of the catheter at the obstruction while the guide wire is withdrawn and until the radial bulge is in contact with the distal end of the catheter. The method can include advancing the catheter 826 in contact with the enlargement 115 together past the obstruction based on the guide wire displacing the distal end of the catheter. The catheter 126 may be a conventional catheter or a catheter configured in accordance with the broad inventive principles disclosed herein.

The method can include rotating the guide wire upon encountering the obstruction to assist in passage past or penetration through the obstruction of the guide wire and catheter. In some embodiments, the rotating the guide wire, for example, when the guide wire has a non-linear portion or bend that allows the tip of the catheter to deflect from the obstacle.

Figure 9B:
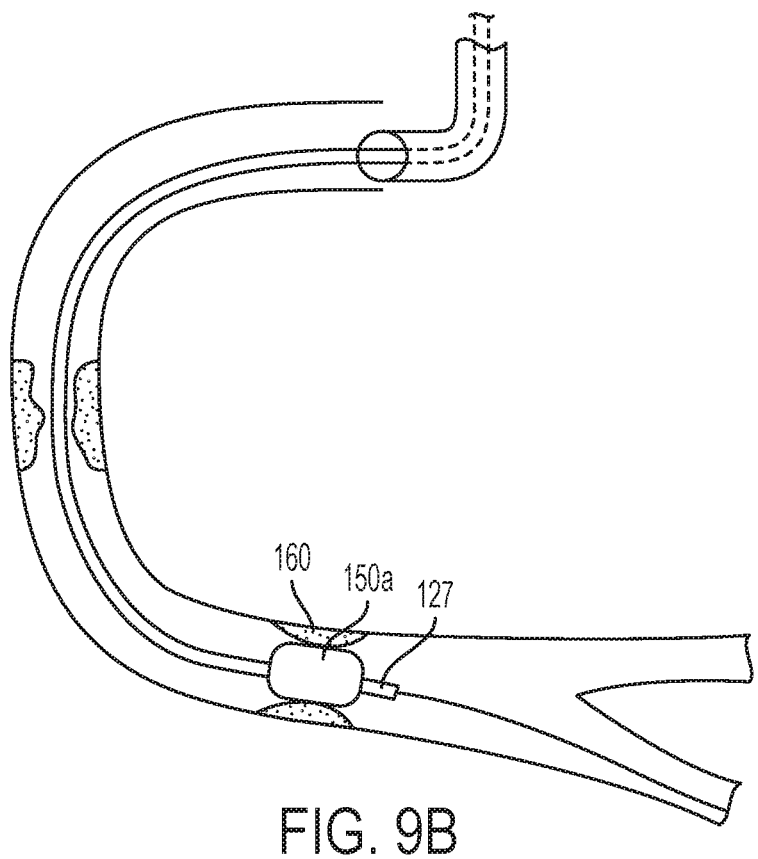
FIG. 9B shows an inflated balloon downstream of a blockage of a vasculature, according to an embodiment of the invention.

FIG. 9B shows that the guide wire system, after having passed through the obstruction 140, can be used to expand a downstream blockage or target 160. Upon reaching the target 160, the balloon 150a can be expanded to outwardly push the target region. FIG. 9B shows that a device, e.g., can be downstream of a blockage of a vasculature. The device can be any interventional device and/or tool such as, but not limited to, a balloon, an inflated balloon, a stent, an atherectomy catheter, etc.

The wire of the guide wire can be configured in combination, or not, with the enlargement. For example, see FIGS.

10A and 10B showing a combination of the wire being configured in addition to the enlargement configuration.

Figure 10A:
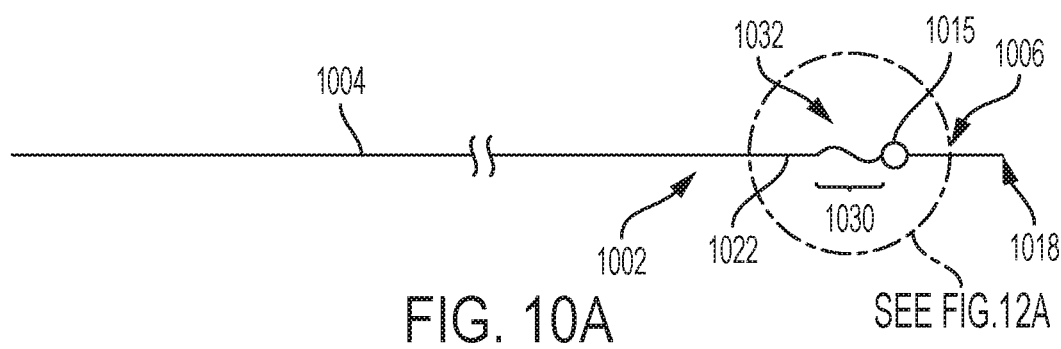
FIG. 10A illustrates a guide wire having a non-linear portion proximal to an enlargement, according to an embodiment of the invention.
Figure 10B:
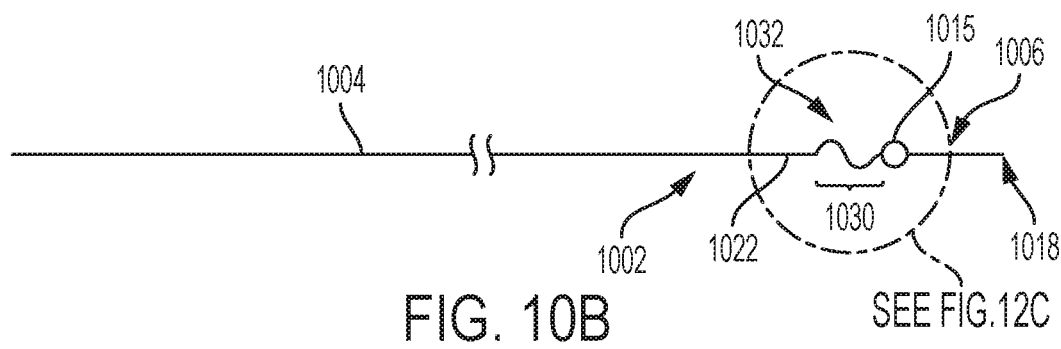
FIG. 10B illustrates a guide wire having a non-linear portion proximal to an enlargement, according to an embodiment of the invention.

As shown in FIG. 10A, the guide wire 1002 can be configured such that there is a non-linear portion 1032 in the elongated member 1004. The non-linear portion 1032 can be at least one of: a curve, a sinusoidal curve, a non-linear section, an angulation, a peak, a valley, a squiggle, curvilinear, and helical section. The non-linear portion can be configured to retract into a catheter, e.g., a catheter tip, to deflect the tip of the catheter away from an obstacle in the vessel. The non-linear portion 1032 can be disposed proximate an enlargement or ball 1015 on a proximal side of the enlargement 1015. The non-linear portion 1032 can have a stiffness coefficient that is greater than the distal portion of the guide wire. The non-linear portion can also have a stiffness coefficient that is less than the proximal portion of the guide wire. In an embodiment, the non-linear portion can have substantially the same stiffness as the guide wire. The stiffness of the non-linear portion can be sufficient enough to prevent substantial straightening in use and/or as the non-linear portion engages the catheter. The stiffness can be varied and/or can be sufficient to cause the catheter tip to move and/or deflect as desired when the configured section of the guide wire engages the catheter tip. In FIG. 10A, a side profile of a planar sinusoidal curve is shown. FIG. 10B shows a side profile of a spiral-shaped helix.

The guide wire can include a non-linear portion that, in some embodiments, can be adjacent to the enlargement. The non-linear section can be proximal to the enlargement 1015. In an embodiment where the non-linear portion is a sinusoidal curve, the non-linear portion can comprise 360 degrees of the sinusoidal curve. In some embodiments, the curve can comprise less than or greater than 360 degrees. The non-linear portion can be about three to five mm in length. A typical balloon is 20 mm is length, therefore a range of the non-linear portion could be between about 3-20 mm. By incorporating the wire configuration of the guide wire in combination with the guide wire enlargement, additional support can be provided to move and/or deflect the catheter tip. In a sinusoidal curve embodiment, the non-linear portion can include three waves or periods to assist in deflecting catheter tip.

In an embodiment, at least one of the non-linear portion and the enlargement can have a hydrophilic coating or is radio-opaque. The non-linear portion can have at least one of a curve, a sinusoidal curve, a non-linear section, an angulation, a peak, a valley, a squiggle, a curvilinear shape, and a helix. The non-linear portion can have a variable stiffness. The non-linear portion can have a stiffness coefficient greater than the remaining portion of the elongated member. The method can include advancing the guide wire with a curve proximate and proximal to the enlargement.

In this manner, the non-linear portion 1032 can affect a distal end 1022 of the elongated member 1004. The non-linear configuration can deflect, move, engage, and/or release the catheter tip, for example. The tip 1006 of the elongated member 1004 can range from three to five mm long. The enlargement 1015 can be disposed immediately proximal to the non-linear portion 1032, as shown in FIG. 10A. A portion of the guide wire extending from the proximal-most portion of the non-linear portion 1032 to the tip 1018 can be of a finer proportion than the elongated member so as to facilitate a flexible leading portion of the guide wire 1002. The guide wire can be made of metal or any other non-deformable material.

FIG. 10B shows an alternative embodiment where the non-linear portion 1032 is helical shaped.

Figure 11A:
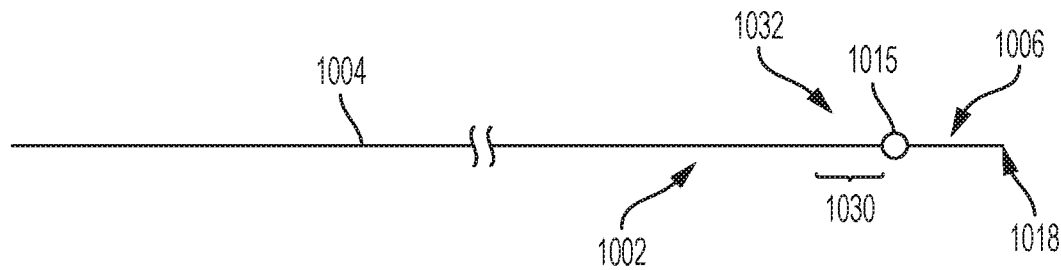
FIG. 11A shows a side view of FIG. 10A, according to an embodiment of the invention.

FIG. 11A shows a side profile of FIG. 10A. As can be seen from FIG. 11A, the non-linear portion 1032 can have a non-linear shape in FIG. 10A, but have a substantially linear shape along its side profile. FIG. 11A, which is a side view of the view of FIG. 10A rotated 90 degrees, is an example of a two-dimensional, not a three-dimensional (spiral) non-linear portion. Thus, the non-linear portion 1032 can have a two-dimensional non-linear shape such that its side profile is straight.

Figure 11B:
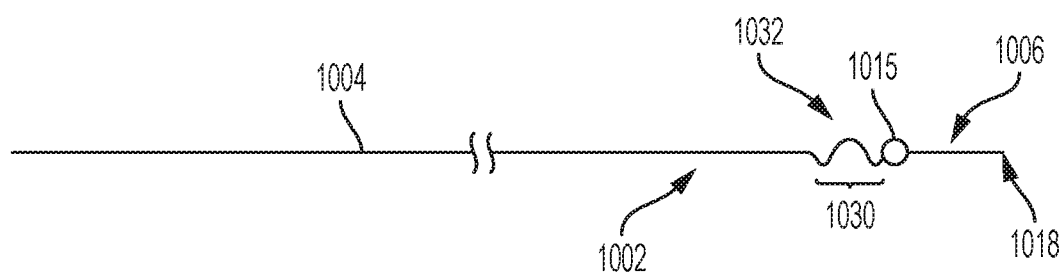
FIG. 11B shows a side view of FIG. 10B, according to an embodiment of the invention.
Figure 11C:
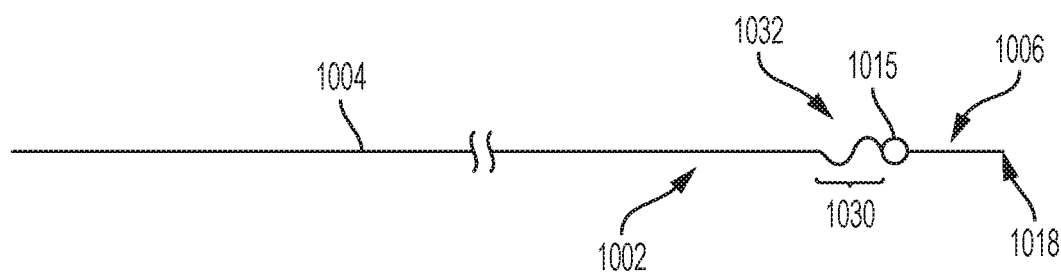
FIG. 11C shows a side view of FIG. 11B further rotated, according to an embodiment of the invention.

In other embodiments, the non-linear portion can have a non-linear shape in any direction, for example, as a helical shape. For example, FIG. 11B, which is a side view of FIG. 10B rotated 90 degrees, is an illustration of the non-linear portion 1032 having a non-linear shape in FIG. 10B, and also have a non-linear shape along its side profile. As shown in FIG. 11B, this would be an example of a three-dimensional (spiral) non-linear portion. Thus, the non-linear portion can have a three-dimensional non-linear shape such that its side profile is also curved. FIG. 11C is a further rotation of FIG. 11B rotated another 90 degrees.

Figure 12C:
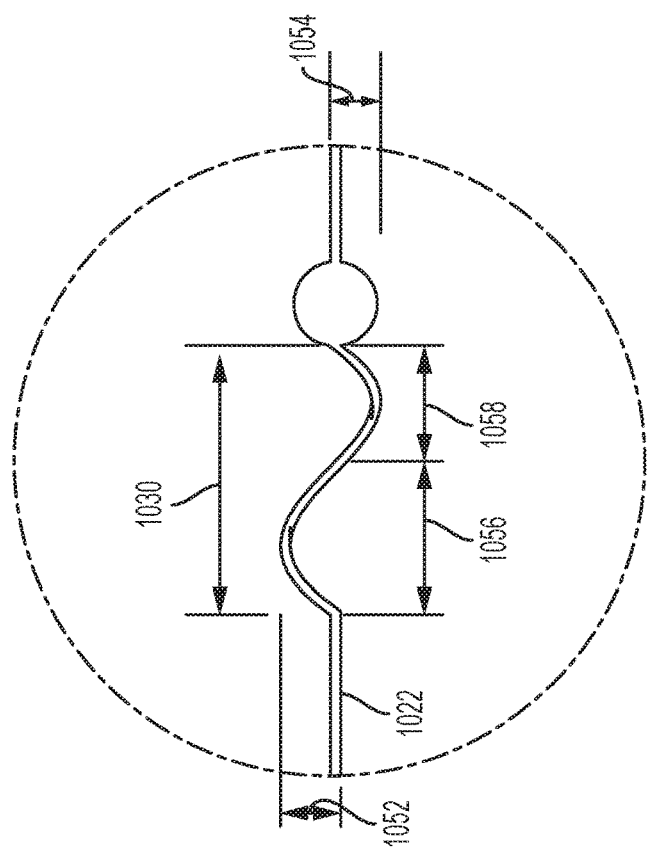
FIG. 12C is a close-up view of a portion of FIG. 10B, according to an embodiment of the invention.
Figure 12D:
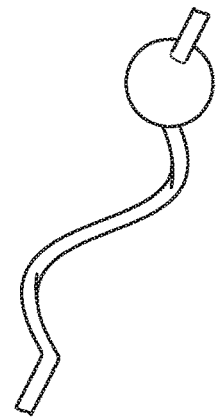
FIG. 12D is a top-right perspective view of FIG. 12C, according to an embodiment of the invention.
Figure 12A:
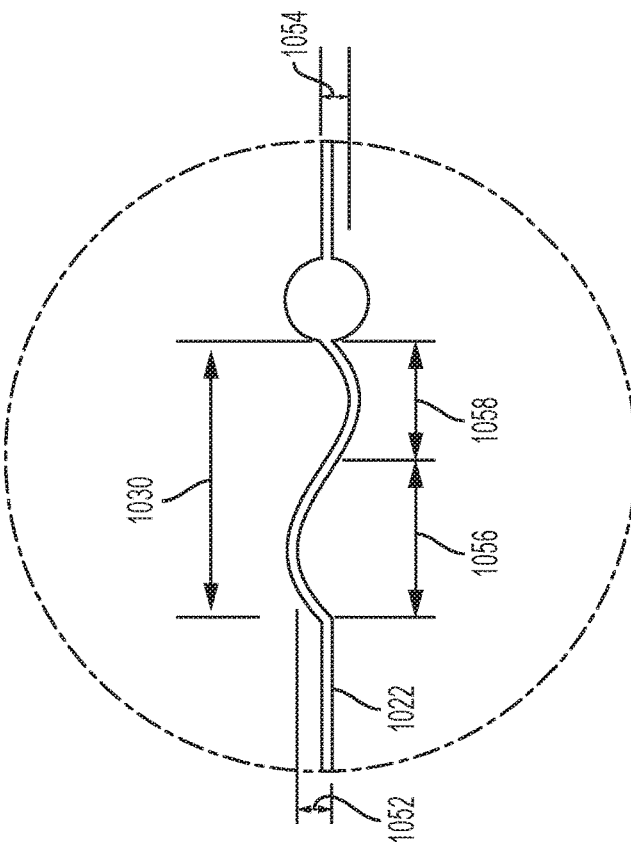
FIG. 12A is a close-up view of a portion of FIG. 10A, according to an embodiment of the invention.
Figure 25:
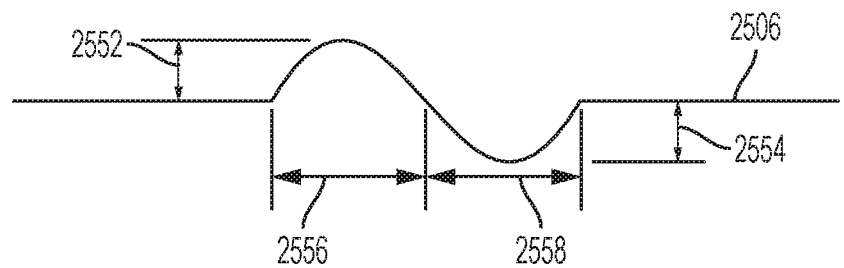
FIG. 25 shows a guide wire having an equally distributed non-linear portion, according to an embodiment of the invention.

FIG. 12A shows a close-up view of the distal region of the guide wire 1002. As can be seen, the non-linear portion 1032 can have a shape of a sinusoidal wave. A first half of the wave can have a distance of 1056 that may be more than half the distance of the entire non-linear portion distance 1030. This first half portion can have a height or amplitude 1052. This first half portion can be viewed as a positive half cycle of the wave when viewed from the perspective of FIG. 12A. In other embodiments, the first half 1056 of the wave can have a distance that is substantially half of the distance, or less than the distance, of non-linear portion distance 1030. For example, FIG. 25 shows an embodiment where the first half portion 2556 can be substantially the same as the second half portion 2558. In this way, the amplitude or height 2552 of the first half portion 2556 can be substantially the same as the amplitude or height of the second half portion 2558. The second half portion 1058 can have a distance of 1058, which can be less than half of the distance of the non-linear portion distance 1030. In other embodiments, the second half of the wave can have a distance that is half or greater than the distance of the non-linear portion distance 1030. This second half portion can have a height or amplitude 1054. The second half portion can be viewed as a negative half cycle of the wave when viewed from the perspective of FIG. 12A.

Even though FIG. 12A shows a positive half cycle first followed by a negative half cycle, other embodiments where a negative half cycle is first followed by a positive half cycle wave form. Also, by rotating the guide wire, the device's arrangement, where a positive half cycle occurs proximally followed by a negative half cycle can be switched to an arrangement where a negative half cycle occurs proximally followed by a positive half cycle with a rotation of the guide wire of 180 degrees.

Figure 12B:
FIG. 12B is a top-right perspective view of FIG. 12A, according to an embodiment of the invention.

FIG. 12B is a cutout, right perspective view of FIG. 12A. FIG. 12B shows that the non-linear portion can proceed along a single plane.

FIG. 12C shows a close-up view of the distal region of the guide wire 1002. As can be seen, the non-linear portion 1032 can have a shape of a spiral or helix. FIG. 12D is a cutout, right perspective view of FIG. 12C. FIG. 12D shows that the non-linear portion can proceed in a helical manner.

Figure 13:
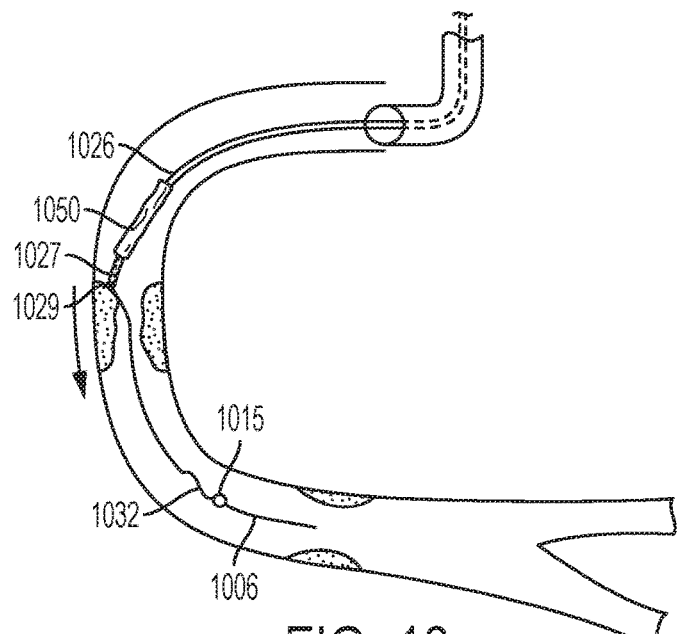
FIG. 13 shows a catheter-guide wire system having a non-linear portion in the guide wire getting caught or stuck at and/or in a blockage of a vasculature, according to an embodiment of the invention.
Figure 14:
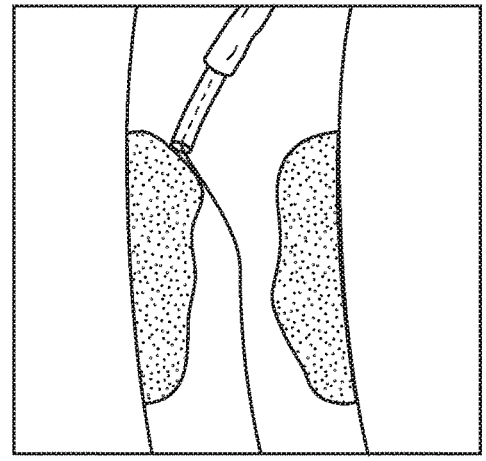
FIG. 14 shows a close-up view of FIG. 13, according to an embodiment of the invention.

FIGS. 13-20 show an alternative embodiment of FIGS. 4-9 where the guide wire system having a non-linear portion is guided through a vasculature. In FIG. 13, the catheter tip 1029 has become stuck on a blockage 1040 while traversing down the vessel. FIG. 14 shows a close-up view of the tip of the catheter in the stuck position.

Figure 15:
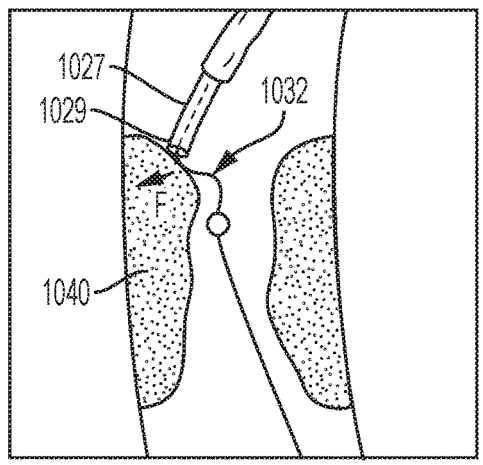
FIG. 15 shows a partially retracted guide wire system having a non-linear portion, according to an embodiment of the invention.
Figure 16:
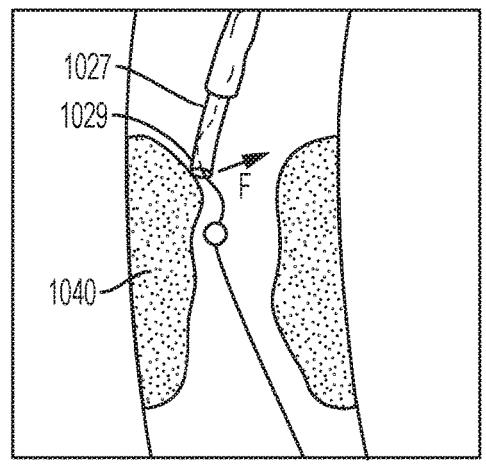
FIG. 16 shows a further retracted guide wire system having a non-linear portion, according to an embodiment of the invention.

FIG. 15 shows the guide wire and the corresponding non-linear portion 1032 retracting back into the catheter. As the guide wire is pulled back into the catheter, the enlargement 1015 can approach the tip 1029 of the catheter 1026. Thereafter, the non-linear portion can exert a force F upon the blockage where the tip 1029 of the catheter 1026 is stuck. In this embodiment, by having the proximal-most half cycle of the non-linear portion be negative with respect to the catheter tip, it can allow a force from the non-linear portion to be exerted on an inner wall of the catheter tip 1029 away from the blockage to spring, pull, release or otherwise allow or cause the catheter tip to move away from the blockage. As the guide wire continues to retract, as shown in FIG. 16, the force F of the movement of the non-linear portion can also be applied to the tip 1029 of the catheter moving it away from the blockage further. The ability to pull the enlargement to the catheter tip, a stop point, can allow the precise positioning of the non-linear portion relative to the catheter tip, and more efficient use of the device.

Figure 28:
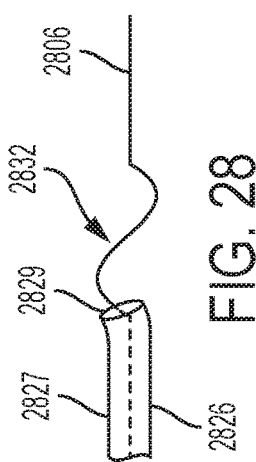
FIG. 28 shows a guide wire catheter system, according to an embodiment of the invention.

In other embodiments, as shown in FIG. 28, a positive proximal-most half cycle of the non-linear portion 2832, with respect to the catheter tip, can also be adapted to move the tip of the catheter away. For example, rather than using the negative half of the non-linear portion to spring the catheter inner wall that is disposed away from the blockage, as is shown in FIG. 15, the distal-most catheter tip 2829 can be moved away by pushing the guide wire into the catheter 2826 and using the curve of the non-linear portion 2832 to guide the catheter tip 2829 in the direction of the curve.

Figure 17:
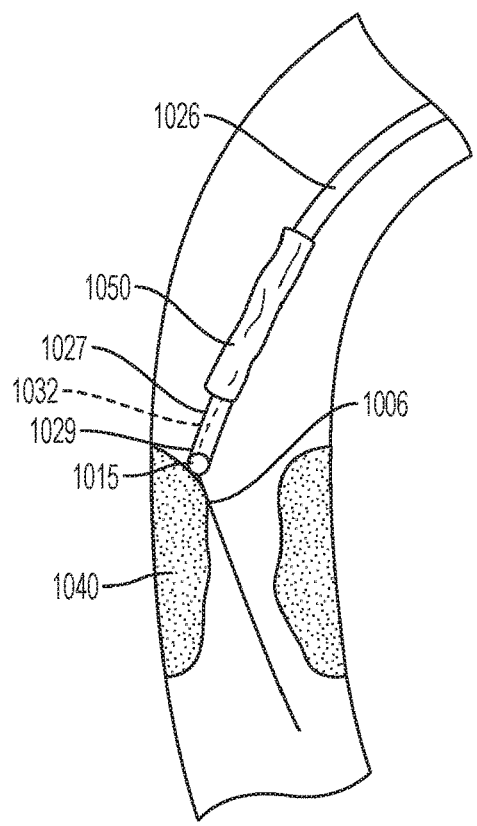
FIG. 17 shows a further completely retracted guide wire system having a non-linear portion, according to an embodiment of the invention.
Figure 18:
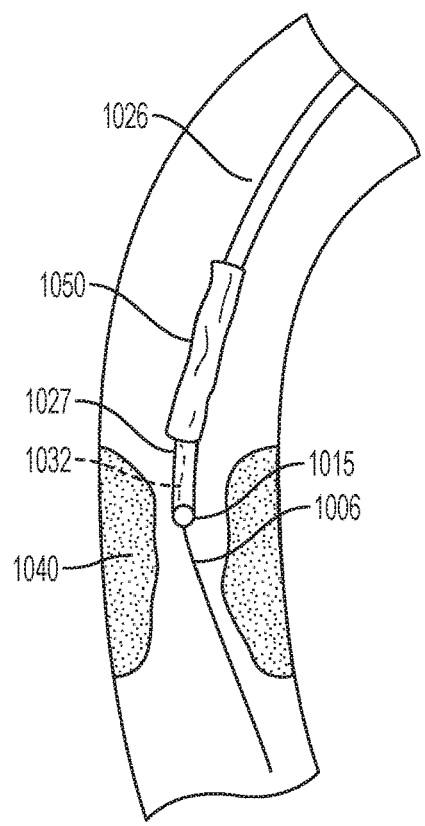
FIG. 18 shows a guide wire system of FIG. 17 after being freed and centrally disposed, according to an embodiment of the invention.
Figure 19:
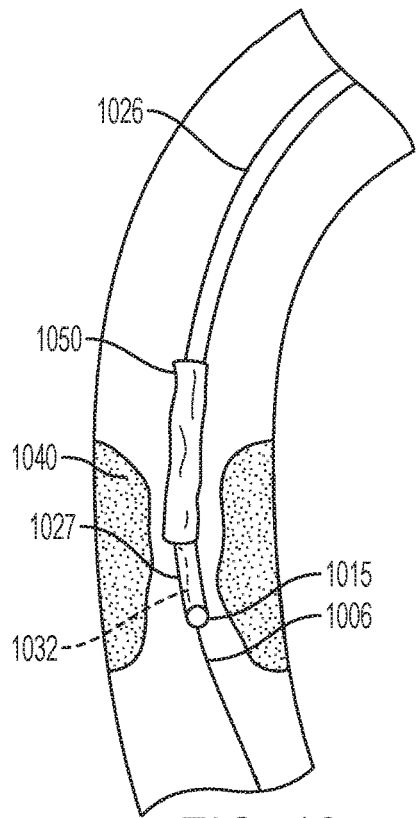
FIG. 19 shows a guide wire system traversing through a blockage of a vasculature, according to an embodiment of the invention.
Figure 20:
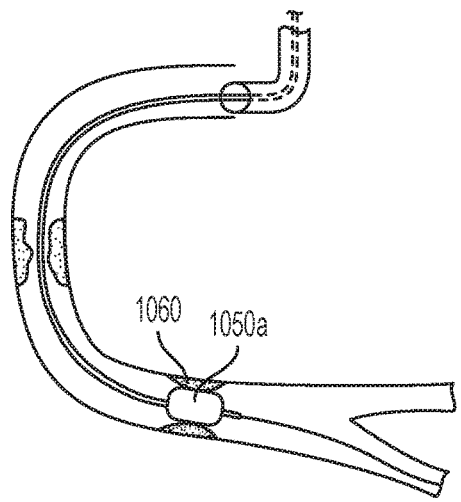
FIG. 20 shows an inflated balloon downstream of a blockage of a vasculature, according to an embodiment of the invention.

FIG. 17 shows the retraction of the guide wire until the enlargement 1015 comes into contact with the catheter tip 1029. As shown, the tip of the catheter has been freed from contact with the blockage. The catheter can position for advancement. As shown, the catheter is in a position centered within the vessel. The catheter can be in a position to proceed past the blockages 1040, as shown in FIG. 18. FIG. 19 shows the guide wire system 1000 traversing down the vessel after been moved and/or centered away from the blockages 1040. After the balloon has reached a target portion 1060, it can be expanded to 1050a.

Figure 21:
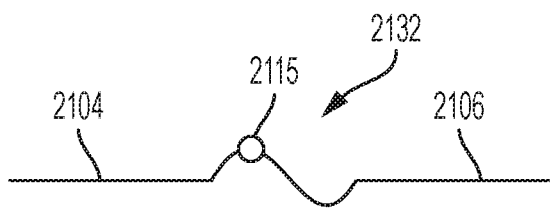
FIG. 21 illustrates a guide wire where an enlargement is located at a non-linear portion, according to an embodiment of the invention.
Figure 22:
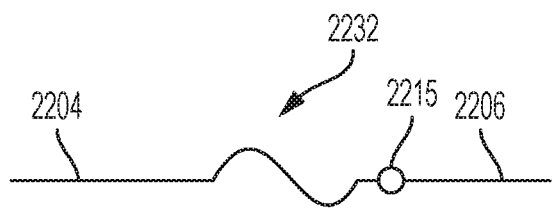
FIG. 22 illustrates a guide wire where an enlargement is distal to a non-linear portion, according to an embodiment of the invention.

An enlargement can also be disposed on the non-linear portion, as shown in FIG. 21. In FIG. 21, the enlargement 2115 is disposed at the height of a bend in the non-linear portion 2132. In other embodiments, as shown in FIG. 22, the enlargement 2215 can be spaced from the non-linear portion 2232 at a distance of, for example, 1 mm or less. Thus, while embodiments have been described and shown where an enlargement borders or is disposed at the non-linear portion, it is contemplated within the inventive principles disclosed herein that the enlargement can be disposed at a distance separate from the non-linear portion. For example, FIG. 22 shows that enlargement 2215 is distal to and spaced apart from non-linear portion 2232. Further, as will be described later, FIG. 24 shows that enlargement 2415a is proximal to and spaced apart from non-linear portion 2432.

Figure 23:
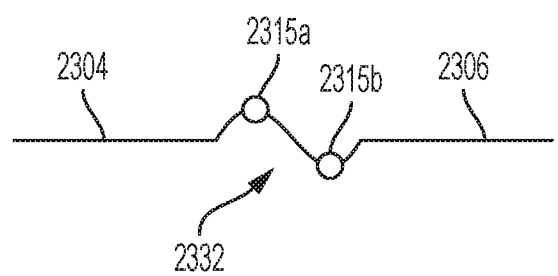
FIG. 23 illustrates a guide wire where two enlargements are on or at a non-linear portion, according to an embodiment of the invention.

In some embodiments, the guide wire can include multiple enlargements. For example, as shown in FIG. 23, enlargements 2315a and 2315b can be disposed at non-linear portion 2332 of guide wire 2304. The guide wire 2302 can thus include more than one enlargement. In some embodiments, having more than one enlargement can facilitate pulling the tip of the catheter from blockages to a greater degree. For example, the guide wire can include a pair of enlargements spaced apart from each other and each disposed at the distal end. In this embodiment, the distal-most enlargement can have an outer diameter that is equal to or smaller than the more proximal enlargement.

Figure 24:
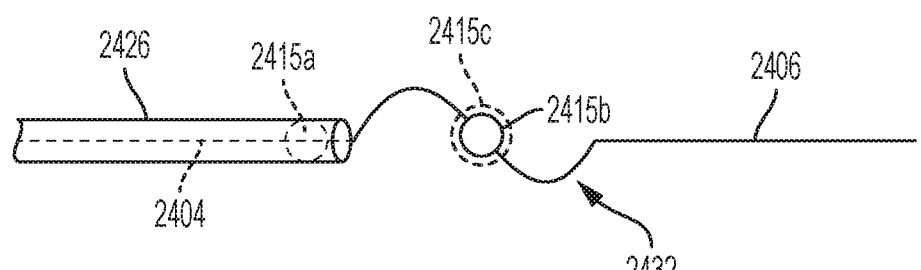
FIG. 24 illustrates a guide wire where a first enlargement is proximally spaced from a non-linear portion and a second enlargement is on or at the non-linear portion, according to an embodiment of the invention.

FIG. 24 describes a guide wire having a first enlargement 2415a disposed at a proximal portion of the guide wire 2404 spaced at or apart from the non-linear portion 2432.

As shown in FIG. 24, a second enlargement 2415b can be disposed distal to the enlargement 2415a, for example, at the non-linear portion 2432. The enlargement 2415a can have a diameter small enough that it can fit inside the catheter 2426. The enlargement 2415b can have a same diameter as enlargement 2415a, but not every enlargement may fit into the catheter. In an embodiment, an enlargement 2415c distal to the proximal enlargement 2415a can have a greater diameter than the proximal enlargement 2415a. In this manner, by being disposed at the non-linear portion 2432 and/or by having a diameter that is larger than the catheter, the distal enlargement 2415b/2415c is not configured to proceed into the catheter. Thus, the tip of the catheter in some embodiments only reaches the most proximal enlargement. The more distal enlargement could work to interface with the vessel wall and/or vessel obstruction, freeing the catheter tip from obstructions.

Figure 26:
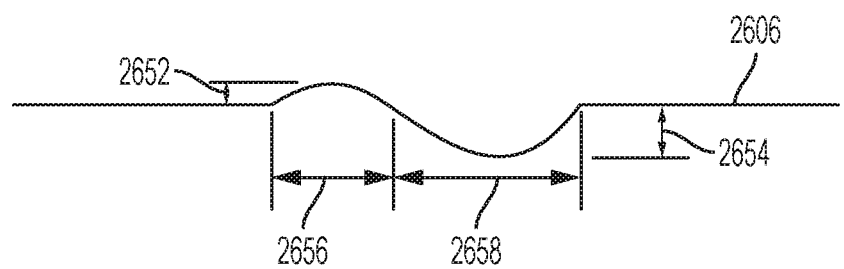
FIG. 26 shows a guide wire having a non-linear portion with a proximal portion more gradual than a distal portion, according to an embodiment of the invention.

FIG. 26 illustrate that the first and second halves can have less amplitude or steepness to the portion. In this embodiment, this can allow the distance 2656 of the first half to be less than the distance 2658 of the second half. Thus, FIG. 26 has a gradual increase to the curvature of the non-linear portion at the proximal end and the curvature is more pronounced in the distal end of the non-linear portion.

Figure 27:
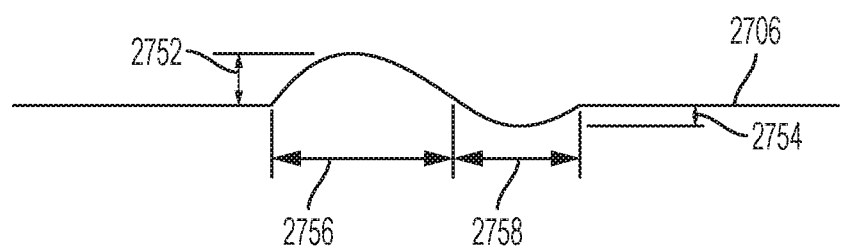
FIG. 27 shows a guide wire having a non-linear portion with a distal portion more gradual than a proximal portion, according to an embodiment of the invention.

FIG. 27 shows an embodiment where the first half 2756 has a more pronounced curvature than the curvature of second half 2758.

Figure 29:
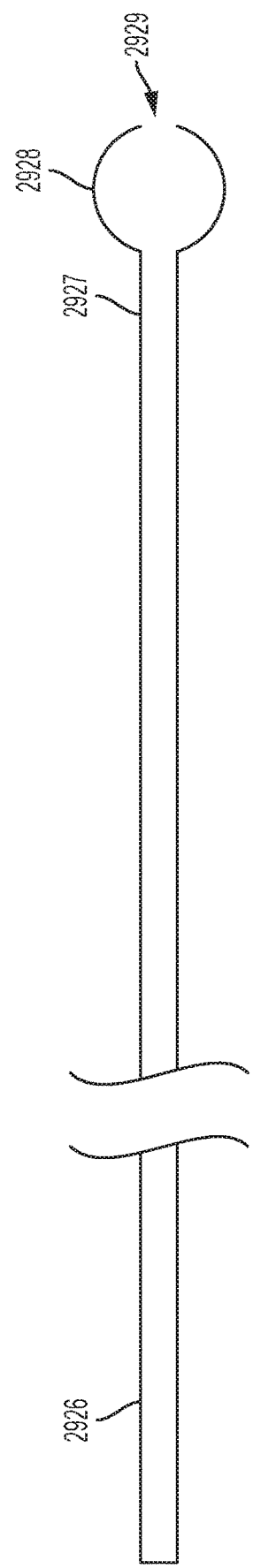
FIG. 29 illustrates a catheter having a bulbous tip, according to an embodiment of the invention.

The catheter in accordance with the principles of embodiments of the invention can be used either with conventional guide wires and/or the guide wire configured in accordance with the principles of embodiments of the invention. As shown in FIG. 29, the catheter can have a bulge 2928 on the tip 2927 of the catheter 2926 with shapes similar to those described and shown in the drawings with respect to the catheters and the guide wires. The bulge 2928 can minimize a likelihood that the catheter becomes stuck on an obstruction in the vessel. Additionally, or alternatively, the bulge 2928 can interact with the enlargement of the guide wire as described with regard to other figures in such a degree that it allows for an even greater degree of pull of the tip. The bulge 2928 of the distal portion of the catheter can be bulb-shaped. An outer diameter of the tip of the distal portion of the catheter can be 30% greater than an outer diameter of the shaft of the catheter.

With a bulge at the distal end of the catheter 2926, the guide wire system in some embodiments can advance through blockages. For example, the curvature in the distal-most portion of the bulge 2928 can make it more difficult for the tip of the catheter to get stuck. This bulge catheter can also be used in conjunction with an enlargement of the guide wire so that upon the catheter becoming stuck in a blockage, the guide wire can be retracted until the enlargement interfaces with the distal end of the bulge of the catheter. The guide wire can proceed through distal exit aperture 2939. The rounded shape of the enlargement coupled with the rounded shape of the bulge of the catheter tip can allow for the catheter to advance past the blockage.

FIG. 28, as also discussed above, shows that the system 2800 can include a catheter 2826 having a shaft and being configured to encompass the guide wire. The catheter 2826 can have a distal portion 2827 where the distal portion 2827 can be configured to interface with a non-linear portion 2832 and/or an enlargement 2815 of the guide wire 2802.

Thus, embodiments of the invention are generally directed to advancing catheter devices in the vasculature. By configuring the guide wire and/or the catheter in accordance with the principles of embodiments of the invention, the catheter tip can be lifted away from the vasculature, for example, lifted away from a resistance in the vasculature. Embodiments of the invention are directed to a guide wire configuration and related methods of using the guide wire. Additionally, embodiments of the invention are directed to a catheter with a configured distal end and/or tip and methods of using the same with a conventional guide wire and/or a guide wire configured in accordance with the principles of embodiments of the invention. The configured guide wire and the configured catheter can be used alone and/or in combination with each other. In one aspect of the invention the guide wire and/or catheter is configured with a focal enlargement to lift a catheter tip away from a resistance in the vasculature.

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

What is claimed is:

1. A system comprising:
   a catheter having a catheter tip, a proximal portion, and a distal portion;
   a guide wire configured for advancing a device having a longitudinal lumen diameter through a vasculature, the guide wire comprising:
   an elongated member having a proximal end and a distal end; and
   an enlargement being disposed on the distal end of the elongated member, the enlargement being spaced proximally from a distal tip of the distal end of the elongated member, the enlargement having a dimension larger than the distal tip and the longitudinal lumen diameter of the device,
   wherein an outer diameter of the enlargement is configured to be greater than an outer diameter of the catheter tip, the enlargement enlarges radially from the catheter tip along a longitudinal axis of the enlargement, and
   wherein the enlargement is adapted to move the device away from an obstruction or the vasculature.

2. The system of claim 1, wherein a portion of the proximal end of the elongated member has a rigidity coefficient greater than a portion of the distal end.

3. The system of claim 1, further comprising a bend in the elongated member, the bend being disposed proximate the enlargement on a proximal side of the enlargement.

4. The system of claim 3, wherein at least one of the bend and the enlargement has a hydrophilic coating or is radio-opaque.

5. The system of claim 3, wherein the bend is at least one of: a curve, a sinusoidal curve, a non-linear section, an angulation, a peak, a valley, a squiggle, curvilinear, and helical.

6. The system of claim 3, wherein the bend has a variable stiffness.

7. The system of claim 3, wherein the bend has a stiffness coefficient greater than the remaining portion of the elongated member.

8. The system of claim 1, wherein the enlargement has a profile that is determined based upon a catheter tip profile and the enlargement is greater than the catheter tip profile.

9. The system of claim 8, wherein the enlargement profile is about 30 percent larger than the catheter tip profile.

10. The system of claim 8, wherein a diameter of the guide wire is 0.014 inches and a diameter of the enlargement is 0.027 inches, when used with a 0.021 inch diameter catheter tip.

11. The system of claim 1, the guide wire further comprising linearly spaced radio-opaque markers to facilitate measurement of a lesion length.

12. The system of claim 1, wherein the enlargement has a radial dimension that is determined based upon the catheter tip outer diameter.

13. The system of claim 1, wherein the enlargement is spherical shaped.

14. The system of claim 1, wherein the enlargement is non-spherical shaped.

15. The system of claim 1, wherein the catheter has a catheter shaft and is configured to encompass the guide wire.

16. The system of claim 15, wherein the guide wire comprises linearly spaced radio-opaque markers to facilitate measurement of a lesion length.

17. The system of claim 15, wherein the enlargement is proximally offset from a distal tip of the distal end of the guide wire.

18. The system of claim 15, wherein the distal portion is enlarged in relation to the catheter shaft, the catheter tip being configured to engage with the enlargement of the guide wire upon the catheter becoming stuck.

19. The system of claim 18, wherein the outer diameter of the catheter tip is 30% greater than an outer diameter of the shaft of the catheter.

20. The system of claim 15, wherein the catheter includes a balloon that protrudes radially from, and extends along, the shaft of the catheter.

21. The system of claim 15, wherein the guide wire has a non-linear portion of at least one of: a curve, a sinusoidal curve, a non-linear section, an angulation, a peak, a valley, a squiggle, curvilinear, and helical.

22. The system of claim 1, wherein the elongated member has a uniform outer diameter and wherein the distal tip of the distal end of the elongated member has a same or smaller outer diameter as the uniform outer diameter of the elongated member.

23. The system of claim 1, further comprising a bend in the elongated member, the bend being disposed proximate the enlargement, wherein the bend is adapted to deflect the device away from the obstruction or the vasculature.

24. The system of claim 23, wherein the bend is disposed at least one of proximal the enlargement, distal to the enlargement, or at the enlargement.

25. The system of claim 1, wherein the enlargement has a profile that is determined based upon a catheter tip profile and the enlargement is greater than the catheter tip profile, and wherein the enlargement is adapted to move the catheter tip away from the obstruction or the vasculature.

26. The system of claim 1, wherein the enlargement shrinks radially at a distance spaced from the catheter tip.

27. The system of claim 1, the enlargement further comprising a proximal end having a first dimension and a distal end having a second dimension, wherein a third dimension located between the proximal end and the distal end is larger than at least one of the first dimension and the second dimension.

28. The system of claim 1, the elongated member further comprising a non-linear portion adjacent the enlargement.

29. The system of claim 1, wherein the enlargement is configured to partially retreat inside the catheter tip.

30. The system of claim 1, wherein the enlargement is configured to not retreat inside the catheter tip.

31. The system of claim 1, wherein the enlargement further comprises multiple enlargements, and wherein the guide wire further comprises a non-linear portion, the multiple enlargements disposed at the non-linear portion.

32. The system of claim 1, wherein the enlargement further comprises multiple enlargements.

33. The system of claim 32, wherein the guide wire further comprises a non-linear portion, wherein at least one of the multiple enlargements is disposed at the non-linear portion.

34. The system of claim 33, wherein at least one of the multiple enlargements is disposed proximate the non-linear portion.

35. The system of claim 1, wherein the enlargement comprises a distal enlargement spaced apart from a proximal enlargement and the proximal enlargement has an outer diameter that is equal to or smaller than the distal enlargement.

36. The system of claim 1, wherein the enlargement comprises a distal enlargement spaced apart from a proximal enlargement and the distal enlargement has an outer diameter that is equal to or smaller than the proximal enlargement.

37. A method of navigating through vasculature, comprising:
advancing a guide wire through a vessel, the guide wire having a substantially uniform outer diameter, and the guide wire having a distal portion that includes a radial bulge;
advancing a catheter over the guide wire, the catheter having a proximal end and a distal end, wherein the radial bulge is larger than the distal end of the catheter;
encountering a vascular obstruction hindering advancement of the catheter; and
withdrawing the guide wire through the catheter to position the radial bulge in contact with the distal end of the catheter,
wherein the step of withdrawing allows the distal end of the catheter to be displaced away from the vascular obstruction to allow advancement of the catheter.

38. The method of claim 37, further comprising the step of:
advancing the catheter in contact with the radial bulge together past the vascular obstruction based on the guide wire displacing the distal end of the catheter.

39. The method of claim 37, further comprising the step of:
advancing the guide wire and the catheter separately past the vascular obstruction.

40. The method of claim 37, further comprising the step of:
maintaining the distal end of the catheter at the vascular obstruction while the guide wire is withdrawn and until the radial bulge is in contact with the distal end of the catheter.

41. The method of claim 37, where the step of withdrawing further comprises withdrawing the radial bulge causing the distal end of the catheter to become unobstructed.

42. The method of claim 37, wherein the step of advancing a guide wire further comprises advancing the guide wire with a curve proximate and proximal to the radial bulge.

43. The method of claim 37, further comprising rotating the guide wire upon encountering the vascular obstruction to assist in passage past or penetration through the vascular obstruction of the guide wire and catheter.

44. The method of claim 37, wherein the radial bulge comprises a proximal radial bulge and a distal radial bulge spaced apart from the radial bulge.

45. The method of claim 44, wherein withdrawing the guide wire through the catheter to position the radial bulge in contact with the distal end of the catheter further comprises withdrawing the proximal radial bulge within the catheter and withdrawing the distal radial bulge in contact with the distal end of the catheter, wherein the distal radial bulge interfaces with the vascular obstruction.

46. A guide wire configured for advancing a device having a longitudinal lumen diameter through a vasculature, the guide wire comprising:
an elongated member having a proximal end and a distal end;
an enlargement being disposed on the distal end of the elongated member, the enlargement being spaced proximally from a distal tip of the distal end of the elongated member, the enlargement having a dimension larger than the distal tip and the longitudinal lumen diameter of the device; and
a sinusoidal curve disposed proximate the enlargement on a proximal side of the enlargement,
wherein an outer diameter of the enlargement is configured to be greater than an outer diameter of a catheter tip, the enlargement enlarges radially from the catheter tip,
wherein the enlargement is adapted to move the device away from an obstruction or the vasculature.

47. The guide wire of claim 46, wherein the enlargement further comprises multiple enlargements.

48. The guide wire of claim 47, wherein at least one of the multiple enlargements is disposed at the sinusoidal curve.

* * * * *